(12) United States Patent
Miyawaki et al.

(10) Patent No.: US 9,249,449 B2
(45) Date of Patent: Feb. 2, 2016

(54) PROBE REAGENT FOR MEASUREMENT OF PROTEOLYTIC ACTIVITY

(75) Inventors: Atsushi Miyawaki, Saitama (JP); Masahiko Hirano, Saitama (JP)

(73) Assignees: Japan Science and Technology Agency, Saitama (JP); Riken, Saitama (JP)

( * ) Notice: Subject to any disclaimer, the term of this patent is extended or adjusted under 35 U.S.C. 154(b) by 0 days.

(21) Appl. No.: 13/574,400

(22) PCT Filed: Jan. 21, 2011

(86) PCT No.: PCT/JP2011/051089
§ 371 (c)(1),
(2), (4) Date: Jul. 20, 2012

(87) PCT Pub. No.: WO2011/090159
PCT Pub. Date: Jul. 28, 2011

(65) Prior Publication Data
US 2012/0288883 A1 Nov. 15, 2012

(30) Foreign Application Priority Data
Jan. 22, 2010 (JP) ................................. 2010-012084

(51) Int. Cl.
*C12Q 1/37* (2006.01)
*C12N 15/85* (2006.01)

(52) U.S. Cl.
CPC *C12Q 1/37* (2013.01); *C12N 15/85* (2013.01); *C07K 2319/00* (2013.01)

(58) Field of Classification Search
None
See application file for complete search history.

(56) References Cited

U.S. PATENT DOCUMENTS

| 7,632,917 B2 * | 12/2009 | Kincaid et al. ................ 530/300 |
| 7,993,879 B2 * | 8/2011 | Tsien et al. ................... 435/69.7 |
| 2004/0265902 A1 * | 12/2004 | Fricker et al. ................. 435/7.1 |
| 2010/0041092 A1 * | 2/2010 | Lin et al. ........................ 435/29 |
| 2010/0086943 A1 * | 4/2010 | Trinquet et al. ............... 435/7.2 |

(Continued)

FOREIGN PATENT DOCUMENTS

| JP | 2007-209227 A | 8/2007 |
| JP | 2007209227 A * | 8/2007 |

(Continued)

OTHER PUBLICATIONS

Orian et al., "Structural motifs involved in ubiquitin-mediated processing of the NF-K B precursor p105: Roles of the glycine-rich region and a downstream ubiquitination domain", Molecular and Cellular Biology, vol. 19, No. 5, pp. 3664-3673, 1999.*

(Continued)

*Primary Examiner* — Robert Mondesi
*Assistant Examiner* — Richard Ekstrom
(74) *Attorney, Agent, or Firm* — Foley & Lardner LLP

(57) ABSTRACT

This invention relates to a probe reagent comprising, in order from the N-terminus to the C-terminus, the amino acid sequences of a fluorescent protein I, a peptide capable of terminating protein degradation (i.e., a degradation-terminating peptide), a spacer peptide, a fluorescent protein II, and a protein to be degraded, wherein the protein to be degraded is a protein degraded by the ubiquitin-proteasome system, and the probe reagent is degraded from the C-terminus, but that the degradation of the probe reagent is terminated at the degradation-terminating peptide, a nucleic acid encoding the probe reagent, and use of the probe reagent or the nucleic acid.

16 Claims, 10 Drawing Sheets

(56) References Cited

U.S. PATENT DOCUMENTS

| | | | |
|---|---|---|---|
| 2010/0151484 A1* | 6/2010 | Vogel et al. | 435/7.1 |
| 2012/0283136 A1* | 11/2012 | Camarero | 506/10 |
| 2012/0322092 A1* | 12/2012 | Tucker et al. | 435/23 |

FOREIGN PATENT DOCUMENTS

| | | |
|---|---|---|
| WO | WO-02/00892 A1 | 1/2002 |
| WO | WO 2012047325 A2 * | 4/2012 |

OTHER PUBLICATIONS

Adams et al., "Proteasome inhibition: a new strategy in cancer treatment", Investigational New Drugs, vol. 18, pp. 109-121, 2000.*

Neefjes et al., "Fluorescent probes for proteolysis: Tools for drug discovery", Nature Reviews: Drug Discovery, vol. 3, pp. 58-69, 2004.*

Tsai et al., "Targeting botulinum neurotoxin persistence by the ubiquitin-proteasome system", Proc. Natl. Acad. Sci. USA, vol. 107, No. 38, pp. 16554-16559, 2010.*

Tian et al., "A conserved processing mechanism regulates the activity of transcription factors Cubitus interruptus and NF-KB", Nature Structural & Molecular Biology, vol. 12, No. 12, pp. 1045-1053, 2005.*

Rape et al., "Taking a bite: proteasomal protein processing", Nature Cell Biology, vol. 4, pp. E113-E116, 2002.*

Zhang et al., "Creating New Fluorescent Probes for Cell Biology", Nature Reviews: Molecular Cell Biology, vol. 3, 906-918, 2002.*

The International Search Report received in the parent application No. PCT/JP2011/051089, dated Mar. 8, 2011.

Orian, A. et al., "Structural Motifs Involved in Ubiquitin-Mediated Processing of the NF-κB Precursor p105: Roles of the Glycine-Rich Region and a Downstream Ubiquitination Domain", *Mol. Cell. Biol.*, 1999, vol. 19, No. 5, pp. 3664-3673.

Asako Sakaue-Sawano et al., "Atarashii Imaging Gijutsu 1. Saibo Shuki o Realtime ni Kashika suru Gijutsu", Experimental Medicine, 2 008, vol.26, No. 17, pp. 2822 to 2829.

Tian, L. et al., "A conserved processing mechanism regulates the activity of transcription factors Cubitus interruptus and NF-kappaB", *Nat. Struct. Mol. Biol.*, 2005, vol. 12, No. 12, pp. 1045-1053.

Extended Supplementary European Search Report dated Jun. 5, 2013, EP 11 73 4765.

Norman L. Lehman, "The ubiquitin proteasome system in neuropathology" ACTA Neuropathol, Jul. 14, 2009, pp. 329-347, vol. 118, No. 3.

* cited by examiner

PROBE REAGENT FOR MEASUREMENT OF PROTEOLYTIC ACTIVITY

TECHNICAL FIELD

The present invention relates to a fluorescent probe reagent for measuring a particular proteolytic activity dependent on the ubiquitin-proteasome system in a living cell.

BACKGROUND ART

The ubiquitin-proteasome system is well known as a proteolytic pathway possessed by cells. In this reaction system, linear chains comprising several molecules of a small protein called ubiquitin are attached to denatured proteins or abnormally folded proteins. The ubiquitin chains can mark the proteins for degradation, which are in turn recognized and destroyed by proteasome, a proteolytic machine. This system performs the removal of intracellular abnormal proteins. The ubiquitin-proteasome system, however, is not always a system intended only for the quality control of intracellular proteins. The system controls various cell functions by degrading even structurally or functionally normal proteins according to cell states of the moment and thereby suppressing their activities. The ubiquitin-proteasome system has been found so far to control the abundances of many proteins. These proteins have diverse functions, such as control of cell cycle, regulation of gene expression, stress response, and DNA repair. In this way, the ubiquitin-proteasome system controls many life phenomena exhibited by cells and is thus considered essential for the maintenance of normal cell activity. Therefore, the hypofunction of this proteolytic system has a critical impact on cells. The abnormal intracellular accumulation or aggregation of proteins is observed in neurodegenerative diseases such as Alzheimer's disease and Parkinson's disease. It has been suggested that the onset of these diseases is caused by the abnormal function of the ubiquitin-proteasome system. Since the ubiquitin-proteasome system is also involved in cell cycle, DNA repair, and the like, the disruption of this system is also known to induce the malignant transformation of cells. In this way, the ubiquitin-proteasome system is responsible for the control of many important life phenomena. Thus, the development of an approach of precisely and conveniently measuring this reaction system would make a significant contribution not only to the elucidation of mechanisms underlying life phenomena exhibited by cells but also to the development of therapy or drugs for diseases induced by abnormality therein.

Protein degradation by the intracellular ubiquitin-proteasome system has previously been measured using a biochemical approach such as Western blotting. In this approach, many cells are collectively destroyed, and their components are recovered. Protein analytes contained therein are electrophoretically separated according to molecular weights and further detected by staining using specific antibodies. As a result, the existing levels of the proteins or proteolytic activities on the proteins can be measured. Unfortunately, this approach requires complicated operation and much time and does not permit assay in individual living cells.

In recent years, great development has been brought about in techniques of applying luciferin and luciferase involved in the bioluminescent reaction seen in firefly or the like, or fluorescent proteins obtained from *Aequorea victoria* or the like, to probe reagents for monitoring intracellular molecular dynamics. Such techniques have been coupled with the advance of microscopic imaging techniques to thereby popularize approaches of spatiotemporally visualizing and measuring a particular physiological activity in cells. This approach has also allowed the proteolytic activity of the proteasome to be measured in living cells. In this approach, a protein analyte is fused with luciferase or a fluorescent protein and used as a probe reagent (Patent Literature 1). When this protein exists in cells, the luminescence or fluorescence which is a label is observed; however, when this protein is degraded by proteasome, the fused luciferase or fluorescent protein is degraded together with the protein, resulting in no observable luminescence or fluorescence. Thus, change in the intensity of this light can be monitored in order to measure a proteolytic activity on this protein. The degradation of proteins such as IκBα, p27, p53, or HIF-1α has been measured so far by this approach (Patent Literature 2 and Non Patent Literatures 1 to 3). Since one type of label, such as luciferase or a fluorescent protein, is used in these probe reagents, the analyte is measured at only one wavelength of luminescence or fluorescence. Therefore, the intensity of the light is influenced by factors independent of proteolytic activity, such as the nonuniform distribution or expression level of the probe reagent, cell or tissue morphology, quenching caused by fading or the like, or nonuniform illumination with excitation light, thereby causing difficulties in quantitative measurements. In addition, when light quantity is decreased by increase of proteolytic activity, the insufficient sensitivity of a detector or a reduced S/N ratio is disadvantageously caused, thereby making precise measurements difficult.

The undesired influence of protein degradation-independent factors in the photometric method using only one wavelength can be canceled by measuring luminescence or fluorescence at two wavelengths and determining the ratio of intensities. In the approach of Davis et al., a protein analyte IκBα fused to click beetle-derived luciferase (CBG68) exhibiting green luminescence was expressed in cells. At the same time, click beetle-derived luciferase (CBR) exhibiting red luminescence was also expressed in these cells. CBG68 exhibits increase or decrease in the amount of its luminescence depending on proteasomal degradation activities on IκBα. On the other hand, the luminescence of CBR is insusceptible to proteasomal degradation and, as such, was used as a control. Davis et al. measured luminescence in a cell group cultured in a multi-well plate, and measured an IκBα-proteolytic activity as a green/red ratio of luminescence intensities in order to correct the difference in the amount of luminescence derived from, for example, different numbers of cells among wells (Non Patent Literature 4). This approach improves quantitative performance compared with the 1-wavelength photometric method, but disadvantageously, can hardly equalize the expression level ratio between two probe molecules, i.e., luminescence intensity ratio, among cells because these two probe molecules are individually expressed. In addition, the luciferase or fluorescent protein used as a label might be nonuniformly distributed in cells, depending on its properties, and thus differ in its localization among the cells. These are responsible for the degraded accuracy of proteolytic activity assay particularly at a single-cell level.

PRIOR ART LITERATURE

Patent Literature

Patent Literature 1: JP Patent Publication (Kokai) No. 2007-209227A (2007)

Patent Literature 2: JP Patent Publication (Kohyo) No. 2004-533224A (2004)

Non Patent Literature

Non Patent Literature 1: Li, X. et al., J. Biol. Chem., Vol. 274, p. 21244-21250, 1999
Non Patent Literature 2: Zhang, G.-J. et al., Nat. Med., Vol. 10, p. 643-648, 2004
Non Patent Literature 3: Rehemtulla, A. et al., Mol. Imaging, Vol. 3, p. 63-68, 2004
Non Patent Literature 4: Davis, R. E. et al., Assay and Drug Development. Technologies, Vol. 5, p. 85-103, 2007

SUMMARY OF INVENTION

Problem to be Solved by Invention

An object of the present invention is to provide a fluorescent probe reagent for measuring a particular proteolytic activity dependent on the ubiquitin-proteasome system in living cells.
Such a probe reagent can overcome the problems of the conventional methods as described in Background Art.

Means for Solution of Problem

In short, the present invention comprises the following characteristics:
(1) A probe reagent comprising, in order from the N-terminus to the C-terminus, the amino acid sequences of a fluorescent protein I, a peptide capable of terminating protein degradation (i.e., a degradation-terminating peptide), a spacer peptide, a fluorescent protein II, and a protein to be degraded, wherein the protein to be degraded is a protein degraded by the ubiquitin-proteasome system, and the probe reagent is degraded from the C-terminus but the degradation of the probe reagent is terminated at the degradation-terminating peptide.
(2) The probe reagent according to (1), wherein the fluorescent protein I and the fluorescent protein II differ in excitation wavelength or fluorescence wavelength, or both.
(3) The probe reagent according to (1) or (2), wherein the fluorescent protein I and the fluorescent protein II are a donor and an acceptor, respectively, of fluorescence energy transfer (FRET).
(4) The probe reagent according to any of (1) to (3), further comprising a nuclear localization signal or a nuclear export signal.
(5) The probe reagent according to any of (1) to (4), wherein the probe reagent comprises one or more degradation-terminating peptides between the fluorescent protein I and the spacer.
(6) The probe reagent according to any of (1) to (5), wherein the spacer peptide is a peptide of one or more amino acids for providing a separation between the degradation-terminating peptide and the fluorescent protein II.
(7) A nucleic acid encoding a probe reagent according to any of (1) to (6).
(8) A vector comprising a nucleic acid according to (7) in an expressible form.
(9) A transformed cell comprising a vector according to (8).
(10) The transformed cell according to (9), wherein the transformed cell is a diseased cell.
(11) A method for screening for a therapeutic agent for a disease associated with abnormality in the ubiquitin-proteasome system, comprising using the probe reagent according to any of (1) to (6), the vector according to (8), or the transformed cell according to (9) or (10) to measure a proteolytic activity of the ubiquitin-proteasome system on the probe reagent in a cell in the presence of a candidate substance which controls proteasome activity.
(12) The method according to (11), wherein the proteolytic activity on the probe reagent is measured on the basis of change in the ratio of fluorescence intensity between the fluorescent proteins I and II.
(13) The method according to (11) or (12), wherein the cell is a diseased cell associated with abnormality in the ubiquitin-proteasome system.
(14) A method for examining the relationship of an abnormality in the ubiquitin-proteasome system with a disease, comprising contacting the probe reagent according to any of (1) to (6) or the vector according to (8) with a cell or a cell extract from a patient with the disease, and measuring a proteolytic activity on the probe reagent.
(15) The method according to (11) or (14), wherein the protein to be degraded in the probe reagent (i.e., a degron protein) is a protein associated with the disease.
The present specification comprises the contents described in the specification and/or drawings of Japanese Patent Application No. 2010-012084 from which the present application claims the priority.

Advantageous Effect of Invention

The present invention provides a probe reagent capable of measuring in real time the proteolytic activity of the ubiquitin-proteasome system in a living cell (also called a "live cell"). This probe reagent has overcome the problems of the conventional probe reagents described in Background Art. By virtue of a degradation-terminating peptide placed between two fluorescent proteins, signals can be obtained from one of the fluorescent proteins even when the reagent is degraded by increased proteolytic activity. This achieves highly accurate measurement or assay even in the presence of increased proteolytic activity. These two fluorescent proteins are present in one molecule and are thus expressed at a quantitative ratio of 1:1 in every cell. As a result, change in their fluorescence intensities can be measured by the ratiometric method to thereby easily and quantitatively compare proteolytic activity among cells. Since the localization of the two fluorescent proteins is always consistent, the distribution of proteolytic activity in cells can be measured accurately. These properties have successfully improved the accuracy, quantitative performance, and convenience of the spatiotemporal assay of proteolytic activity.

MODE FOR CARRYING OUT THE INVENTION

A probe reagent of the present invention is constituted of proteins and structurally has a form in which five factors, i.e., a fluorescent protein I, a peptide capable of terminating protein degradation, a spacer peptide for providing a separation between this degradation-terminating peptide and a subsequent fluorescent protein II, the fluorescent protein II, and a protein to be degraded, are linked in this order from the N-terminus. This probe reagent is degraded from the C-terminus when proteolytic activity increases, but the degradation of the probe reagent is terminated at the degradation-terminating peptide. As a result, the fluorescent protein I remains intact, while the fluorescent protein II disappears by this degradation. Thus, change in their fluorescence intensities can be monitored in order to measure the proteolytic activity.

A characteristic of the probe reagent of the present invention is that this probe reagent can be used for measuring the proteolytic activity of the ubiquitin-proteasome system in a living cell.

The proteasome is a proteolytic machine possessed by cells. It has a barrel-like structure containing protease active sites in its lumen. The protein to be degraded by the proteasome is modified by polyubiquitination by the action of ubiquitin ligase or the like. The proteasome recognizes this marked protein and incorporates the protein into the lumen with its three-dimensional structure unfolded so that the protein is destroyed into peptides of several amino acids.

Not all proteins recognized by the proteasome are completely destroyed as described above. Some proteins are known to be degraded only at a limited site and escape the degradation of the whole molecule. For example, p105 protein, a component of the transcription factor NFκB, is distributed, with its transcriptional activity suppressed, in the cytoplasms of resting cells. Upon stimulation with activation signals, this protein is ubiquitinated. Approximately C-terminal half of its structure is destroyed by the proteasome, while the remaining N-terminal part is released as a protein called p50 without being degraded. This p50 then transfers to the nucleus and promotes gene transcriptional activity. Specifically, NFκB virtually utilizes proteasomal degradation activity for the ON/OFF control of its transcriptional activity.

Tian et al. (Nat. Struct. Mol. Biol., Vol. 12, p. 1045-1053, 2005) has reported that for terminating this proteasomal protein degradation in the middle thereof, it is structurally required that a sequence called simple sequence where identical amino acids are continuously arranged should precede a tightly folded domain, which is a strong three-dimensional structure, in the direction of proteasome movement. In the case of p105, a portion called glycine-rich region (GRR) where glycine appears with high frequency corresponds to the simple sequence, and a Rel homology domain corresponds to the tightly folded domain (Tian, L. et al., supra).

Figure 1:
FIG. 1 shows the structure of a probe reagent of the present invention.

The probe reagent of the present invention utilizes such limited proteasomal degradation reaction which terminates protein degradation in the middle thereof. The present inventors combined a fluorescent protein having a β barrel structure, which would serve as the tightly folded domain, with a peptide having the simple sequence to prepare a probe reagent that terminated proteasomal degradation in the middle thereof. This probe reagent comprises five regions: two fluorescent proteins differing in excitation or fluorescence wavelength, or both, a peptide which halts degradation, a spacer peptide for providing a separation between the degradation-terminating peptide and the subsequent fluorescent protein, and a protein to be degraded by the proteasome (referred to as a "degron protein"). The probe reagent assumes a structure in which these five regions are linked in the form of one amino acid strand. These regions are arranged as follows: the fluorescent protein I, the degradation-terminating peptide, the spacer peptide, the fluorescent protein II, and the degron protein in this order from the N-terminus (FIG. 1). For example, when the fluorescent proteins I and II used in the probe reagent differ in fluorescence wavelengths, this reagent maintains its full length without degradation of the degron protein and can thus exhibit 2-wavelength fluorescence emission. Once the degron protein is degraded, the fluorescent protein II linked to the N-terminus thereof then disappears by this degradation. This degradation, however, is terminated by the degradation-terminating peptide located on the N-terminal side thereof. As a result, the fluorescent protein I remains intact without being degraded, so that only its fluorescence is observed. Thus, change in the fluorescence intensities of these 2 wavelengths can be determined to thereby assay the proteolytic activity on the degron protein.

Green fluorescent protein (GFP) obtained from *Aequorea victoria* or its variants, or other fluorescent proteins obtained from various organism species including coral or their variants, for example, fluorescent proteins known in the art such as GFP, EGFP, CFP, YFP, ECFP, YPet, CyPet, Venus, mCherry, Cerulean, mKeima, T-Sapphire, Midoriishi-Cyan, or Kusabira-Orange, can be used as fluorescent proteins without limitations (Current Protocols in Cell Biology, 2006; 21.5.1-21.5.33 (John Willy & Sons); J. Endocrinol. 2001; 170: 297-306; and Bioorganic & Medicinal Chemistry Letters 2009; 19: 3748-3751). The fluorescent proteins I and II used largely differ in excitation or fluorescence wavelength, or both so that the proteolytic activity on the degron protein can be measured on the basis of change in the fluorescence intensities of 2 wavelengths.

In the structure of this probe reagent, the fluorescent proteins I and II are positioned close enough to cause fluorescence energy transfer (FRET). Once the fluorescent protein II disappears along with the degradation of the degron protein, FRET is canceled. Thus, a pair that can serve as a donor and an acceptor in FRET can be used as the fluorescent proteins to determine the proteolytic activity also from change in the amount of FRET. Change in the amount of FRET also changes the fluorescence intensities of the donor and the acceptor at the time of donor excitation. Thus, for example, when the fluorescent proteins I and II are used as a donor and an acceptor, respectively, change in the amount of FRET can be measured on the basis of change in the ratio of fluorescence intensities between the fluorescent proteins I and II at the time of the excitation of the fluorescent protein I. It is also known that the fluorescence life of the donor is shorter in the presence of FRET than in the absence thereof Thus, the fluorescent protein I can be used as a donor to determine the proteolytic activity on the degron protein also from change in the fluorescence life. Examples of the fluorescent proteins serving as a donor-acceptor pair include: cyan fluorescent protein (CFP) and yellow fluorescent protein (YFP); and Midoriishi-Cyan and Kusabira-Orange.

Possible regions that could terminate the proteasomal degradation of p105, which is a protein to be degraded in a limited manner, were searched for peptides for terminating the degradation of the probe reagent (hereinafter, the amino acid Nos. of human p105 will be described according to Accession number NM_003998, human NFB1 transcript variant 1; in addition, NM_001165412 (human NFB1 transcript variant 2), NM_008689 and NM_001159394 (both, mouse homologs), and the like are known). The human p105 protein is composed of 969 amino acids. Upon activation, approximately C-terminal half of this protein, as described above, is degraded by the proteasome, while N-terminal 435 amino acids are released as a protein called p50 without being degraded. This degradation is terminated at a point called processing point. GRR (glycine-rich region), which corresponds to the simple sequence, is a region of amino acids 376-404 from the N-terminus and contains a cluster of 19 glycine residues (Orian, A. et al., Mol. Cell. Biol., Vol. 19, p. 3664-3673, 1999). Thus, the present inventors investigated whether this GRR and its neighboring sequence functioned as a degradation-terminating peptide by which degradation was terminated before reaching the fluorescent protein, and consequently found that: GRR alone failed to terminate the degradation; and a sequence positioned on the C-terminal side of GRR was further required for terminating the degradation. It was also found that the amino acid sequence flanking on the C-terminal side of GRR was not necessarily required to be derived from p105. These results demonstrated that a peptide sequence for providing a separation between the C-terminus of GRR and the fluorescent protein II was required for protecting this probe reagent from further proteasomal degradation. In this context, the GRR moiety was designated as a degradation-terminating peptide, while the sequence flanking on the C-terminal side thereof was designated as a spacer peptide. It was further found that the degradation was not terminated if 10 or more amino acids were inserted between the N-terminus of GRR and the fluorescent protein I.

Such peptides capable of terminating degradation may be any other proteins that are degraded by proteasome in a limited manner, as in p105. Examples of such proteins include, but are not limited to, p100 (transcription factor, NFκB component), cubitus interruptus (*Drosophila* transcription factor; e.g., NM_079878, NM_001081125 (mouse homolog), NM_005270 (human homolog)), EBNA-1 (Epstein-Barr virus protein), Spt23 (yeast transcription factor; e.g., NC_001143, NM_001179586, NC_006029, EU861367), and Mga2 (yeast transcription factor; e.g., NM_001179555, NC_001141, NC_006029, CP000499) (Rape, M. and Jentsch, S., Nat. Cell Biol., Vol. 4, E113-E116, 2002) (note: all accession numbers described herein are GenBank accession numbers). In addition, any of GRR-like peptides derived from these proteins may be used as the degradation-terminating peptide. Such a degradation-terminating peptide can have the following features (a) to (d):

(a) The degradation-terminating peptide consists of a peptide containing 70% or more (in terms of component ratio) of amino acids having 0 to 3 carbon atoms in the side chain, such as glycine, alanine, serine, aspartic acid, and asparagine.
(b) One or more degradation-terminating peptides may be arranged between the fluorescent protein I and the spacer.
(c) The spacer peptide is a peptide for providing a separation between the degradation-terminating peptide and the fluorescent protein II and contains one or more amino acids, for example, consists of 1 to 200 amino acids, preferably, 2 to 100 amino acids, more preferably 5 to 50 amino acids.
(d) The number of amino acids located between the fluorescent protein I and the degradation-terminating peptide is less than 10 amino acids, which may be zero (0).

The degron protein is a protein, as an analyte, that is degraded by the ubiquitin-proteasome system. Many proteins are known to be degraded by proteasome. This region can be replaced by the degron protein of interest, thereby allowing the probe reagent of the present invention to utilize in the assay of the proteolytic activity thereon with general versatility. Examples of the proteins degraded by the ubiquitin-proteasome system include, but are not limited to, proteins known in the art such as Cyclin (A, B, D, and E), p53, Aβ, p27, p21, p16, p15, p18, p19, p62, IκB, NF-κβ, c-fos/c-jun, c-myc, β-catenin, E2F-1, p130, cdc25, tyrosine amino transferase, Polo-like kinase, topoisomerase 1, Smad, Notch, Nrf2, HIF-1α, and Geminin (Adams, J. et al., Invest. New Drugs, 18, 109-121, 2000; and Nakano, T et al., Acta Neuropathol. (Berl), 107: 359-364, 2004). The full-length structure of the degron protein may be used. Alternatively, only a moiety essential for the degradation of the protein, for example, a moiety receiving ubiquitination, a moiety receiving modification such as phosphorylation necessary for the induction of ubiquitination, in each molecule may be used. Cells recognize the probe reagent as a foreign molecule. Therefore, for preventing the introduction of the probe reagent into a cell from causing unnecessary disturbance in the activity of the cell, it is preferred to comprise only the structure necessary for degradation as the degron protein and exclude the other active regions.

As described above, abnormality in the ubiquitin-proteasome system is associated with various diseases. For example, neurodegenerative diseases, cancers (or tumors), ischemic diseases (e.g., infarction), inflammatory diseases, and allergic diseases are known as such diseases. Of these diseases associated with such abnormality, the neurodegenerative diseases, such as Alzheimer's disease and Parkinson's disease, occur because the degron proteins are hardly susceptible to proteasomal degradation (JP Patent Publication (Kokai) No. 2009-149524A (2009), JP Patent Publication (Kokai) No. 2008-222603A (2008), etc.). Thus, proteasome activators probably serve as therapeutic agents therefor. On the other hand, cancer occurs as a result of proteasomal degradation of the degron protein (JP Patent Publication (Kokai) No. 2007-254320A (2007)). Thus, proteasome inhibitors probably serve as therapeutic agents therefor.

The probe reagent of the present invention can be used for measuring the proteolytic reaction of the ubiquitin-proteasome system possessed by cells. Since this degradation system is ubiquitously present in eukaryotic cells, all types of cells can be used as analytes. Such cells also include cells associated with abnormalities in the ubiquitin-proteasome system, for example, neurons, tumor cells, lymphocytes, skin cells, and joint synovial cells.

Since the probe reagent of the present invention is constituted only of proteins, a nucleic acid(s) (e.g., gene(s), DNA(s), or messenger RNA(s)) encoding its amino acid sequence(s) can be introduced into cells and used in assay or measurement after the expression of the probe reagent by the cells. The proteasome is known to be distributed in the nucleus and the cytoplasm. The probe reagent can be expressed in a form tagged with a signal sequence that causes expression in a manner localized only to the nucleus (nuclear localization signal), or a signal sequence that causes expression in a manner localized only to the cytoplasm (nuclear export signal), to thereby selectively measure the proteolytic activity on the degron protein in this site. Known nuclear localization signals and nuclear export signals as described in literatures, etc., can be used. The introduction of DNA or RNA into cells can be performed by a general approach such as lipofection, electroporation, or microinjecton.

The nucleic acid encoding the probe reagent of the present invention can be prepared, for example, by obtaining DNAs encoding the proteins and the peptides constituting the probe reagent by cloning or PCR known in the art and ligating these DNAs in order, followed by PCR amplification. For the cloning, the nucleic acid is inserted in an expressible form into an appropriate vector, which can in turn be cloned into cells such as E. coli, fungi, plant cells, or animal cells. The vectors are, for example, plasmids, phages, cosmids, and viruses. Various vectors and cloning systems according to purposes are commercially available from Takara Bio Inc., Invitrogen Corp., Applied Biosystems, Inc., and the like, and can be used conveniently. For the expression of the nucleic acid, an expression cassette containing ligation of regulatory sequences such as a promoter, an enhancer, a replication origin, a ribosome-binding site, a terminator, a polyadenylation site can be formed and inserted into the multicloning site of each vector. Techniques such as gene recombination, transformation, transfection, and PCR are described in, for example, Sambrook et al., Molecular Cloning: A Laboratory Manual, Cold Spring Harbor Laboratory Press, second ed. (1989); and Ausubel et al., Short Protocols in Molecular Biology, John Wiley & Sons (2002) and can be used for the present invention.

In addition to the approach of allowing cells to transiently express the probe reagent as described above, cells carrying the nucleic acid and stably expressing the probe reagent may be prepared and used in assay or measurement. Furthermore, transgenic non-human organisms (e.g., non-human animals) containing this nucleic acid introduced therein can be prepared in order to measure the proteolytic activity at a whole-body level. In this case, the nucleic acid may be ligated downstream of an appropriate promoter and selectively expressed in the organ or tissue of interest of a non-human animal for use in assay or measurement.

The non-human animals can be prepared according to an approach known in the art involving, for example, introducing the nucleic acid in an expressible form into animal-derived embryonic stem (ES) cells or induced pluripotent stem (iPS) cells, then introducing the ES or iPS cells into embryos at the blastocyst stage, and transplanting the embryos into the uteri of foster animals, which are in turn allowed to give birth to obtain chimeric non-human animals and further, their progeny.

When the fluorescent proteins I and II largely differ in excitation wavelength from each other and have almost equal fluorescence wavelengths, the fluorescence of this probe reagent is measured by a 2-wavelength excitation/1-wavelength fluorescence photometric method comprising switching the excitation wavelengths. Examples of such fluorescent proteins include T-Sapphire (excitation peak: 399 nm, fluorescence peak: 511 nm) and EGFP (excitation peak: 488 nm, fluorescence peak: 507 nm). Alternatively, when the fluorescent proteins I and II have almost equal excitation wavelengths and largely differ in fluorescence wavelength, a 1-wavelength excitation/2-wavelength fluorescence photometric method comprising switching the fluorescence wavelengths is performed for the measurement. Examples of such fluorescent proteins include Cerulean (excitation peak: 433 nm, fluorescence peak: 475 nm) and mKeima (excitation peak: 440 nm, fluorescence peak: 620 nm). Measurement using FRET also corresponds to this 1-wavelength excitation/2-wavelength fluorescence photometric method. Alternatively, when the fluorescent proteins I and II largely differ in both excitation and fluorescence wavelengths, a 2-wavelength excitation/2-wavelength fluorescence photometric method comprising switching these two excitation wavelengths and two fluorescence wavelengths is performed for the measurement. Examples of such fluorescent proteins include Venus (excitation peak: 515 nm, fluorescence peak: 528 nm) and mCherry (excitation peak: 587 nm, fluorescence peak: 610 nm).

In any case, fluorescence can be measured at two wavelengths. As a result, the proteolytic activity can be measured by the ratiometric method to determine change in their fluorescence intensities. The ratiometric method can cancel change in fluorescence intensity caused by protein degradation-independent factors such as different distribution of the probe reagent within cells, nonuniform illumination with excitation light, or fading of fluorescence and can thus achieve more quantitative measurement.

A microscopic imaging system comprising a fluorescence microscope connected to a detector such as a cooled CCD camera can be used for measurement at a single-cell level using the probe reagent of the present invention. According to measurement modes, a filter changer, a monochromator, or the like is connected behind a light source, for switching excitation wavelengths. Alternatively, a filter changer, a 2-wavelength spectrometer for imaging, or the like is connected before a detector, for monitoring fluorescence at 2 wavelengths. Also, dual-band fluorescence microscopic filters and dichroic mirrors suitable for the wavelength characteristics of the two fluorescent proteins used are used for monitoring fluorescence at 2 wavelengths and may be used in combination with a color camera. In this case, the proteolytic activity on the degron protein can be imaged as change in color and thus easily detected. In addition, a confocal laser scanning microscope, a multiphoton-excited microscope, or the like may be used as a microscopic imaging system. When it is desired to obtain data from many cells without the need of resolution at a single-cell level, the measurement may be performed using a fluorescence spectrophotometer, a plate reader, flow cytometry, etc. A macroscopic imaging apparatus using a black box can be used for measurement at a whole-body level.

With regard to the application of the probe reagent of the present invention, the reagent can be used in the medical field, for example, as follows:

The ubiquitin-proteasome system degrades many proteins. This means that the ubiquitin-proteasome system is deeply involved in diverse life activities. Abnormality in this system is responsible for many diseases. For example, adult T-cell leukemia, Crohn's disease, cancer of each organ, rheumatoid arthritis, xeroderma pigmentosum, Fanconi anemia, Cockayne syndrome, Alzheimer's disease, Parkinson's disease, amyotrophic lateral sclerosis, and Huntington's chorea are known as diseases associated allegedly with abnormality in the ubiquitin-proteasome system. The degron protein moiety can be replaced by any of these proteins to utilize the probe reagent of the present invention with general versatility. Moreover, the probe reagent of the present invention can be expected to contribute to the development of therapy or therapeutic agents for these diseases by measuring proteolytic activity on a protein causative of the disease or a protein associated with the disease as the degron protein in cells or animal bodies.

Thus, the present invention further provides a method for screening for a therapeutic agent for a disease associated with abnormality in the ubiquitin-proteasome system, comprising using the probe reagent, the vector, or the transformed cell to measure the proteolytic activity of the ubiquitin-proteasome system on the probe reagent in a cell in the presence of a candidate substance which controls a proteasome activity.

The disease associated with abnormality in the ubiquitin-proteasome system is, for example, neurodegenerative diseases, cancers (or tumors), ischemic diseases (e.g., infarction), inflammatory diseases, or allergic diseases, as exemplified above. Such abnormality accompanies the abnormal control of proteasome activity. For example, proteasome activators may serve as therapeutic agents for neurodegenerative diseases, while proteasome inhibitors may serve as therapeutic agents for cancers or ischemic diseases (e.g., infarction) (JP Patent Publication (Kohyo) No. 2002-541206A (2002), JP Patent Publication (Kohyo) No. 2001-511814A (2001), JP Patent Publication (Kohyo) No. 2008-525427A (2008), etc.).

In this test system, the probe reagent or the vector of the present invention is contacted with a cell or a transformed cell, particularly, a cell associated with abnormality in the ubiquitin-proteasome system, and a candidate substance to thereby select a substance controlling (i.e., increasing or suppressing (or inhibiting)) the proteolytic activity of the ubiquitin-proteasome system contained in the cell on the probe.

In this system, the proteolytic activity on the probe reagent can be measured on the basis of, for example, change in the ratio of fluorescence intensities between the fluorescent protein I and the fluorescent protein II.

The present invention further provides a method for examining the relationship of an abnormality in the ubiquitin-proteasome system with a disease, comprising contacting the probe reagent or the vector with a cell or a cell extract from a patient with the disease and measuring a proteolytic activity on the probe reagent.

In this method, a normal cell or a cell extract of the normal cell is used as a control. The abnormality in the ubiquitin-proteasome system can be associated with a disease by comparison with results of the control using the probe reagent or the vector of the present invention. Such a disease can be selected from the diseases exemplified above.

In this method, the degron protein in the probe reagent is a protein associated with the disease, for example, a protein known in the art such as Cyclin (A, B, D, or E), p53, Aβ, p27, p21, p16, p15, p18, p19, p62, IκB, NF-κβ, c-fos/c-jun, c-myc, β-catenin, E2F-1, p130, cdc25, Tyrosine amino transferase, Polo-like kinase, Topoisomerase 1, Smad, Notch, Nrf2, HIF-1α, or Geminin.

EXAMPLES

Hereinafter, the present invention will be described more specifically with reference to Examples. However, the scope of the present invention is not intended to be limited to these Examples.

Example 1

<Screening for Degradation-Terminating Peptide>

Figure 2:
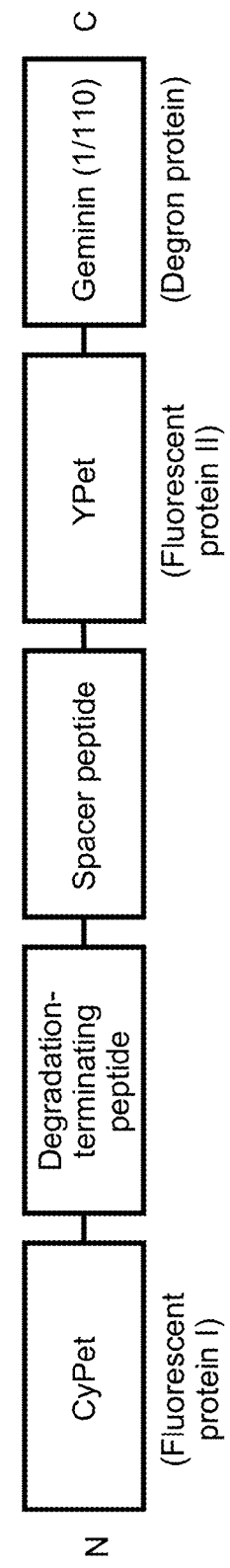
FIG. 2 shows the structure of a probe reagent for search for a degradation-terminating peptide.

In order to develop a probe reagent of interest, p105 was screened for a peptide sequence capable of terminating degradation. CyPet as a fluorescent protein I, YPet as a fluorescent protein II, and Geminin as a degron protein were used to prepare an experimental probe reagent (FIG. 2). The fluorescent protein CyPet is derived from CFP and has an excitation wavelength peak of 435 nm and a fluorescence wavelength peak of 477 nm. The fluorescent protein YPet is derived from YFP and has an excitation wavelength peak of 517 nm and a fluorescence wavelength peak of 530 nm. This pair is known to efficiently cause FRET with CyPet as a donor and YPet as an acceptor. The protein Geminin is a factor controlling the progression of cell cycle and has the function of inhibiting the licensing of DNA replication (Cell 1998; 93 (11): 1043-1053; and Am. J. Pathol. 2002; 161 (1): 267-273). Its abundance is strictly controlled during cell cycle so that its expression level increases in the $S/G_2/M$ phases and this protein disappears due to the promoted degradation by the ubiquitin-proteasome system in the $G_1$ phase. A region of N-terminal amino acids 1-110 (Geminin (1/110)) containing a moiety necessary for the degradation of the Geminin molecule was selected from the structure of Geminin (e.g., NM_015895 (human, SEQ ID NOs: 18 and 19), NM_020567 (mouse)) and used in this experiment.

The respective cDNAs of these molecules were amplified by PCR and ligated by insertion to each restriction enzyme site in the multicloning site of a cloning vector pBluescript II SK(+) (Stratagene) to prepare gene DNA of the probe reagent. A region of amino acids 366-440 in human-derived p105 (SEQ ID NOs: 16 and 17) was screened for a peptide sequence for terminating degradation. This region contains GRR and processing point.

Figure 3:
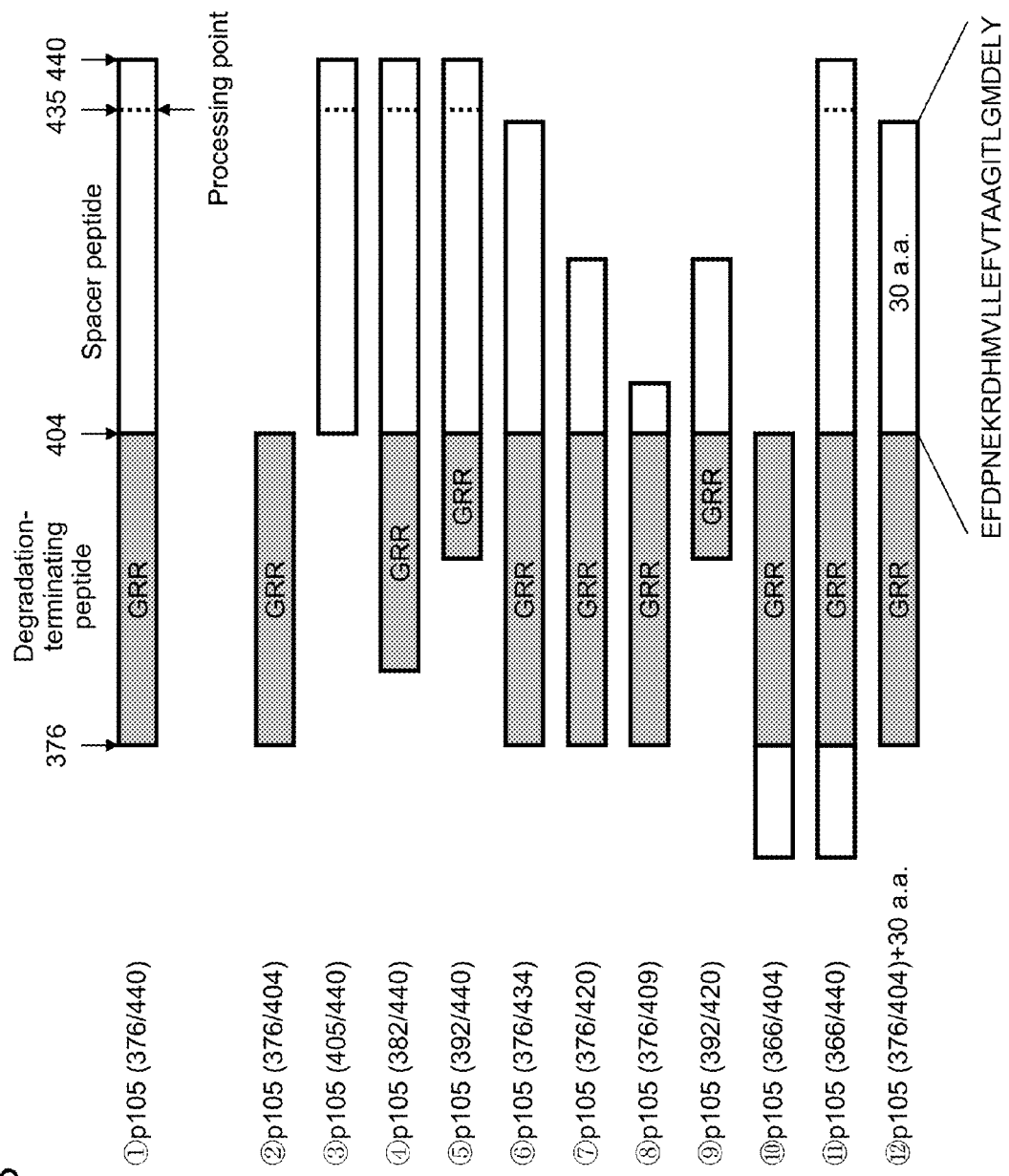
FIG. 3 shows the sites of p105 used as a degradation-terminating peptide and a spacer peptide.

FIG. 3 shows a schematic diagram thereof (where the term "p105 (m/n)" represents a peptide consisting of amino acids m to n from the N-terminus of p105). The prepared gene DNA of the probe reagent was then excised from the pBlueScript vector with restriction enzymes, and this fragment was inserted into the multicloning site of an expression vector CSII-EF-MCS to prepare a vector for expression in cultured cells.

HeLa cells were cultured in a Dulbecco's modified Eagle's medium containing 10% fetal bovine serum in a 35 mmφ glass-bottomed dish. The prepared vector plasmid was mixed with a transfection reagent FuGENE (Roche Applied Science) and added to the medium. The HeLa cells were cultured in a $CO_2$ incubator for 2 days so that the cells expressed the probe reagent and experienced cell cycle.

As a result of cell observation under fluorescence microscope, bright fluorescence was observed in the nuclei of many cells. This is because the intramolecular nuclear localization signal of the Geminin protein, which functions in the nucleus, allowed the probe reagent to be selectively incorporated into the nucleus. The amount of Geminin changes periodically depending on the promoted or suppressed degradation by the ubiquitin-proteasome system in accordance with cell cycle. If the degradation of the probe reagent accompanying the degradation of Geminin is terminated by the degradation-terminating peptide, CyPet accumulates in the cell during every cell cycle without being degraded and thus reduces an YPet/CyPet fluorescence intensity ratio serving as an index value for FRET at the time of CyPet excitation. After the degradation of Geminin, the probe reagent lacks the nuclear localization signal. As a result, the remaining CyPet molecule also becomes distributed in the cytoplasm. The cells were fluorescently imaged from these viewpoints and screened for a peptide capable of terminating degradation.

An inverted microscope (IX70, Olympus Corp.) was used in cell observation. Fluorescence images were obtained using a 3-CCD cooled color camera (ORCA-3CCD, Hamamatsu Photonics K.K.). This camera can simultaneously capture images in three wavelength (red, green, and blue) regions and merge them to form observable color images. Also, it can individually measure the brightness of the image in each wavelength region. After excitation with a 440 nm band-pass filter, the fluorescence images of the cells were obtained through a 460 nm long-pass filter. This setting achieves the simultaneous observation of fluorescence images based on CyPet and YPet at the time of CyPet excitation. The fluorescence emission of CyPet is seen mainly in the blue region and partially in the green region according to its spectral characteristics. By contrast, the fluorescence emission of YPet is mostly seen in the green region. Since the brightness of images in the blue and green wavelength regions was derived from CyPet and YPet, respectively, the fluorescence intensity ratio therebetween was determined for FRET. Moreover, after excitation with a 490 nm band-pass filter, fluorescence images were obtained through a 510-560 nm band-pass filter. Since this setting achieves the observation of fluorescence in the green wavelength region at the time of direct excitation of YPet, the presence and localization of YPet were confirmed. The brightness of images was analyzed using an image analyzer AQUACOSMOS (Hamamatsu Photonics K.K.).

Figure 4:
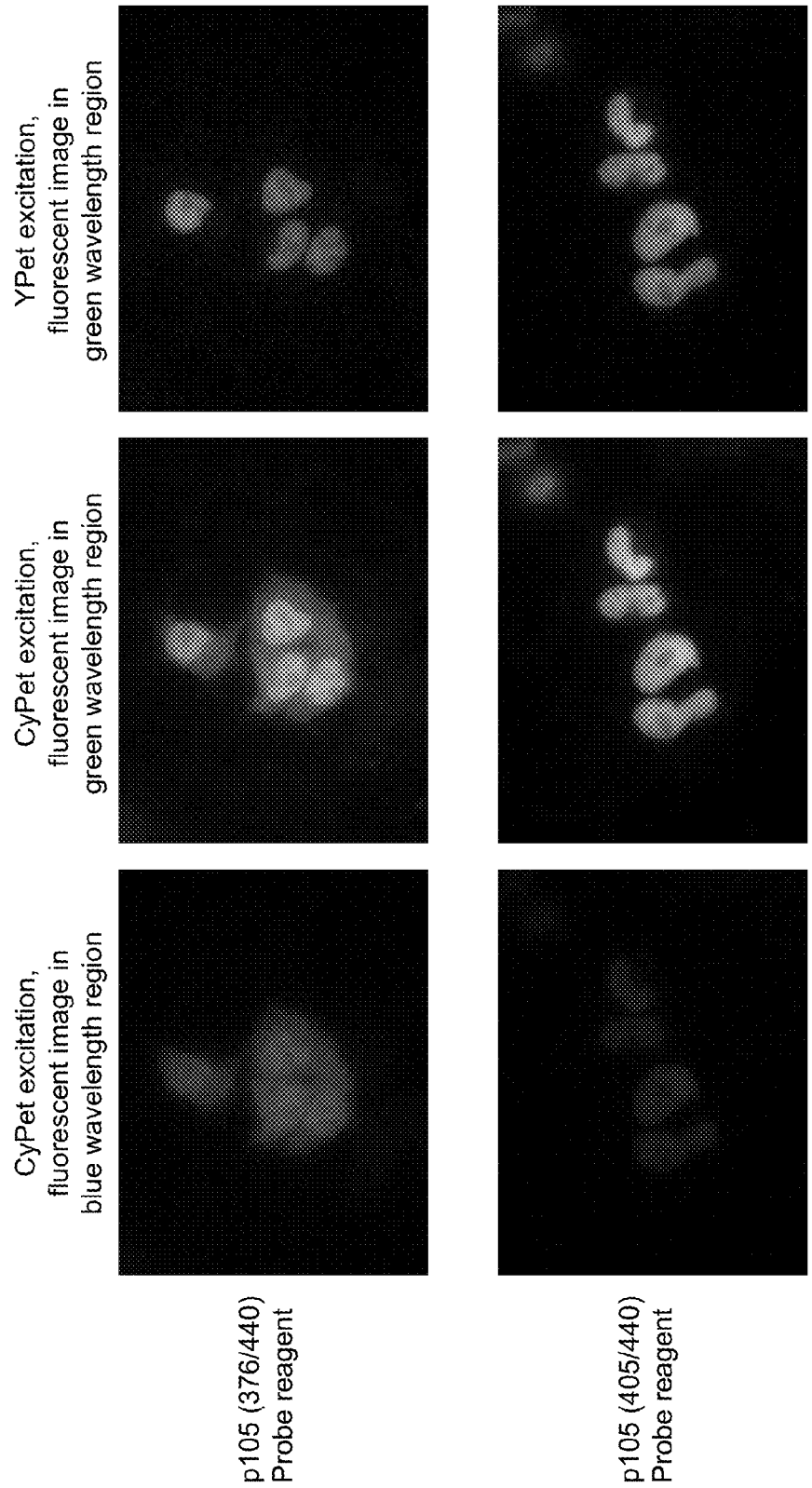
FIG. 4 shows fluorescent observation examples of the probe reagent for search for a degradation-terminating peptide.
Figure 5:
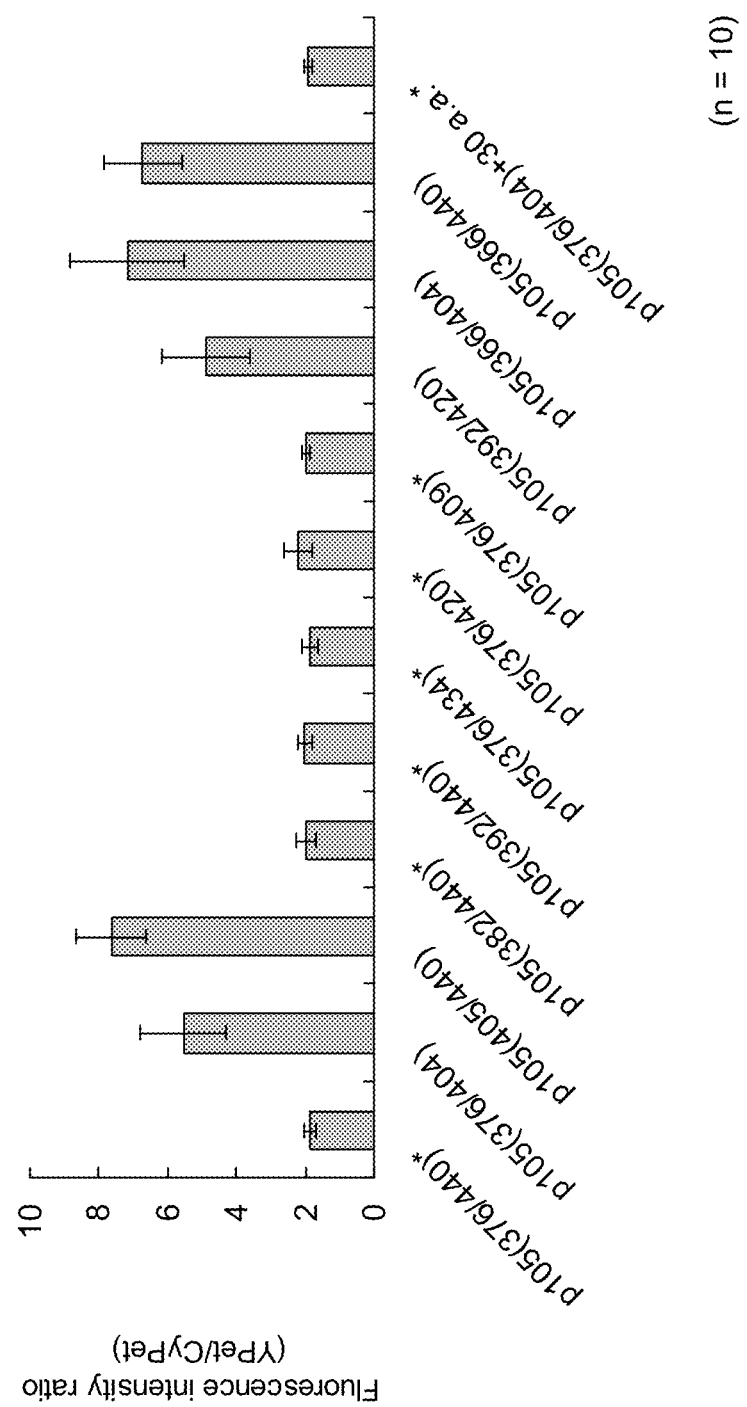
FIG. 5 shows the results of FRET assay of the probe reagent for search for a degradation-terminating peptide. In this figure, * represents that fluorescence was observed not only in the nucleus but also in the cytoplasm.

FIG. 4 shows observation examples of cells expressing the probe reagent containing p105 (376/440) or p105 (405/440) as a peptide for terminating degradation. For the p105 (405/440) probe reagent, fluorescence was distributed only in the nuclei of all observed cells. Only weak fluorescence was observed in the blue wavelength region at the time of CyPet excitation, whereas strong fluorescence was observed in the green wavelength region, indicating that strong FRET from CyPet to YPet occurred. The YPet/CyPet fluorescence intensity ratio at the time of CyPet excitation was 7.64±1.03 (mean±standard deviation). By contrast, for the p105 (376/440) probe reagent, relatively strong fluorescence was observed in some cells even in the blue wavelength region at the time of CyPet excitation. The fluorescence intensity ratio of these cells was 1.87±0.17, which was significantly lower than the value of the p105 (405/440) probe reagent, suggesting that FRET was canceled (FIG. 5). For the p105 (376/440) probe reagent, fluorescence attributed to CyPet excitation was also observed in the cytoplasm. Upon direct excitation of YPet, fluorescence was observed only in the nucleus. Thus, the fluorescence seen in the cytoplasm was probably derived from CyPet. These results demonstrated that the p105 (376/440) sequence was able to terminate the degradation of the probe reagent accompanying the degradation of the degron protein.

Similar results to those obtained in p105 (376/440) were also confirmed in the probe reagents containing p105 (382/440), p105 (392/440), p105 (376/434), p105 (376/420), or p105 (376/409) as a peptide for terminating degradation, demonstrating that some peptides comprising the whole or partial sequence of GRR combined with a sequence flanking on the C-terminal side thereof were capable of efficiently terminating protein degradation just before the fluorescent protein. Similar results were also obtained in the peptide p105 (376/404) +30 a.a. in which the amino acids flanking on the C-terminal side of GRR were replaced by a sequence of 30 amino acids near the C-terminus of CyPet, demonstrating that the amino acid strand added to GRR did not have to be derived from p105. In this context, the 30 a.a. is shown in SEQ ID NO: 15. These results demonstrated that GRR and the peptide sequence located on the C-terminal side thereof as a spacer for providing a separation between GRR and the fluorescent protein II were required for terminating the degradation of the probe reagent. Also, the results about p105 (366/440) demonstrated that the degradation was not terminated if 10 amino acids were inserted between the N-terminus of GRR and the fluorescent protein I.

Hereinafter, the amino acid sequence of each degradation-terminating peptide+spacer peptide confirmed by this experiment to be capable of terminating the degradation of the probe reagent will be shown together with the nucleotide sequence of its DNA.

p105 (376/440)
Amino acid sequence of positions 376-440 in human p105
Degradation-terminating peptide: positions 376-404 (underlined), Spacer peptide: positions 405-440
(SEQ ID NO: 1)
GGGSGAGAGGGGMFGSGGGGGTGSTGPGYSFPHYGFPTYGGITFHPGTT

KSNAGMKHGTMDTES

Nucleotide sequence
(SEQ ID NO: 2)
GGCGGTGGTAGTGGTGCCGGAGCTGGAGGCGGAGGCATGTTTGGTAGTGG

CGGTGGAGGAGGGGGCACTGGAAGTACAGGTCCAGGGTATAGCTTCCCAC

ACTATGGATTTCCTACTTATGGTGGGATTACTTTCCATCCTGGAACTACT

AAATCTAATGCTGGGATGAAGCATGGAACCATGGACACTGAATCT p105 (382/440)
Amino acid sequence of positions 382-440 in human p105
Degradation-terminating peptide: positions 382-404 (underlined), Spacer peptide: positions 405-440
(SEQ ID NO: 3)
GAGGGGMFGSGGGGGTGSTGPGYSFPHYGFPTYGGITFHPGTTKSNAGM

KHGTMDTES

Nucleotide sequence
(SEQ ID NO: 4)
GGAGCTGGAGGCGGAGGCATGTTTGGTAGTGGCGGTGGAGGAGGGGGCAC

TGGAAGTACAGGTCCAGGGTATAGCTTCCCACACTATGGATTTCCTACTT

ATGGTGGGATTACTTTCCATCCTGGAACTACTAAATCTAATGCTGGGATG

AAGCATGGAACCATGGACACTGAATCT p105 (392/440)
Amino acid sequence of positions 392-440 in human p105
Degradation-terminating peptide: positions 392-404 (underlined), Spacer peptide: positions 405-440
(SEQ ID NO: 5)
GGGGGGTGSTGPGYSFPHYGFPTYGGITFHPGTTKSNAGMKHGTMDTES Nucleotide sequence
(SEQ ID NO: 6)
GGCGGTGGAGGAGGGGGCACTGGAAGTACAGGTCCAGGGTATAGCTTCCC

ACACTATGGATTTCCTACTTATGGTGGGATTACTTTCCATCCTGGAACTA

CTAAATCTAATGCTGGGATGAAGCATGGAACCATGGACACTGAATCT p105 (376/434)
Amino acid sequence of positions 376-434 in human p105
Degradation-terminating peptide: positions 376-404 (underlined), Spacer peptide: positions 405-434
(SEQ ID NO: 7)
GGGSGAGAGGGGMFGSGGGGGTGSTGPGYSFPHYGFPTYGGITFHPGTT

KSNAGMKHG

Nucleotide sequence
(SEQ ID NO: 8)
GGCGGTGGTAGTGGTGCCGGAGCTGGAGGCGGAGGCATGTTTGGTAGTGG

CGGTGGAGGAGGGGGCACTGGAAGTACAGGTCCAGGGTATAGCTTCCCAC

ACTATGGATTTCCTACTTATGGTGGGATTACTTTCCATCCTGGAACTACT

AAATCTAATGCTGGGATGAAGCATGGA

-continued p105 (376/420)
Amino acid sequence of positions 376-420 in human p105
Degradation-terminating peptide: positions 376-404 (underlined), Spacer peptide: positions 405-420
(SEQ ID NO: 9)
<u>GGGSGAGAGGGGMFGSGGGGGGTGSTGPG</u>YSFPHYGFPTYGGITF Nucleotide sequence
(SEQ ID NO: 10)
<u>GGCGGTGGTAGTGGTGCCGGAGCTGGAGGCGGAGGCATGTTTGGTAGTGG CGGTGGAGGAGGGGGCACTGGAAGTACAGGTCCAGGG</u>TATAGCTTCCCAC

ACTATGGATTTCCTACTTATGGTGGGATTACTTTC p105 (376/409)
Amino acid sequence of positions 376-409 in human p105
Degradation-terminating peptide: positions 376-404 (underlined), Spacer peptide: positions 405-409
(SEQ ID NO: 11)
<u>GGGSGAGAGGGGMFGSGGGGGGTGSTGPG</u>YSFPH Nucleotide sequence
(SEQ ID NO: 12)
<u>GGCGGTGGTAGTGGTGCCGGAGCTGGAGGCGGAGGCATGTTTGGTAGTGG CGGTGGAGGAGGGGGCACTGGAAGTACAGGTCCAGGG</u>TATAGCTTCCCAC

AC p105 (376/404) + 30 a.a.
Sequence comprising 30 amino acids near the C-terminus of CyPet added to the amino acid sequence of positions 376-404 in human p105
Degradation-terminating peptide: positions 376-404 (underlined) in p105, Spacer peptide: glutamic acid + phenylalanine + amino acids 211-238 of CyPet
(SEQ ID NO: 13)
<u>GGGSGAGAGGGGMFGSGGGGGGTGSTGPG</u>EFDPNEKRDHMVLLEFVTAAG

ITLGMDELY

Nucleotide sequence
(SEQ ID NO: 14)
<u>GGCGGTGGTAGTGGTGCCGGAGCTGGAGGCGGAGGCATGTTTGGTAGTGG CGGTGGAGGAGGGGGCACTGGAAGTACAGGTCCAGGG</u>GAATTCGACCCCA

ACGAGAAGCGCGATCACATGGTCCTGCTGGAGTTCGTGACCGCCGCCGGG

ATCACTCTCGGCATGGACGAGCTGTAC

The release of the fluorescent protein I to the cytoplasm along with the progression of cell cycle was also observed for the combinations of Venus and mCherry, AmCyan and mCherry, TurboGFP and TurboRFP, and mAzami-Green and mKusabira-Orange used as the fluorescent protein I and the fluorescent protein II, respectively, in the probe reagents containing Geminin (1/110) as a degron protein and p105 (376/440) as a degradation-terminating peptide+spacer peptide. This result suggests that many types of fluorescent proteins can be applied as components to this probe reagent.

Example 2

<Time-Lapse Imaging of Probe Reagent Comprising Geminin (1/110) as Degron Protein>

HeLa cells were allowed to express a probe reagent comprising the peptide p105 (376/440) (degradation-terminating peptide p105 (376/404)+spacer peptide p105 (405/440)) shown to be capable of terminating degradation, CyPet and YPet as fluorescent proteins I and II, respectively, and Geminin (1/110) as a degron protein, and time-lapse imaged to measure a change in fluorescence over time accompanying cell cycle.

The measurement was conducted using an incubator fluorescence microscope (LCV110, Olympus Corp.). After excitation with LED at 455 nm, the fluorescence images of CyPet and YPet were obtained with a cooled CCD camera through a 460-510 nm band-pass filter and a 515-560 nm band-pass filter, respectively. In addition, YPet was directly excited with LED 505 nm, and its images were obtained through a 528-555 nm band-pass filter. Each image was obtained every 30 minutes for 48 hours. The brightness was analyzed for each of the nucleus region and the other cytoplasm region to assay an YPet/CyPet fluorescence intensity ratio at the time of CyPet excitation.

Figure 6:
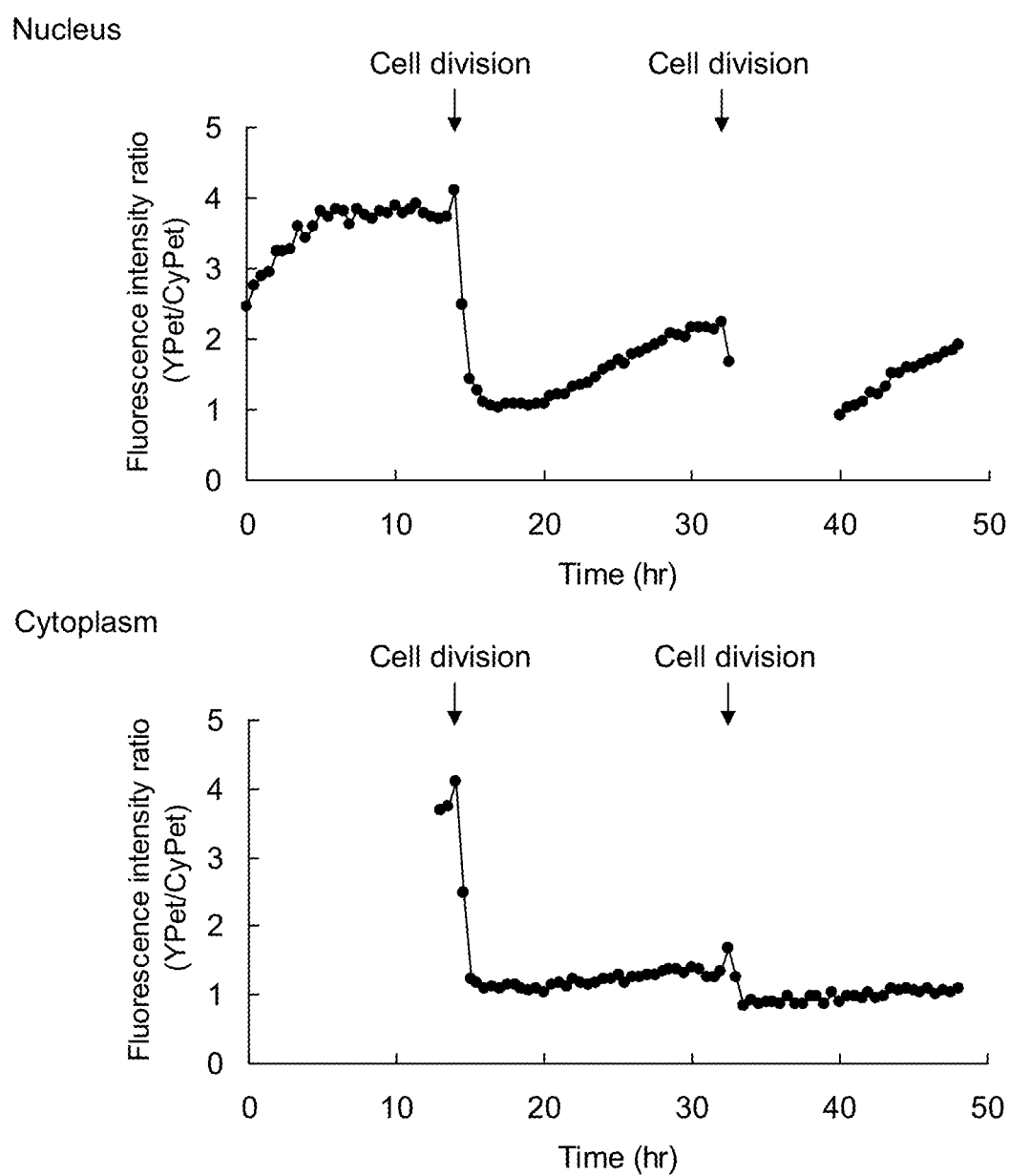
FIG. 6 shows the time-dependent change in the fluorescence intensity ratio of a Geminin degron probe reagent in the nucleus and the cytoplasm of a cell.
Figure 7:
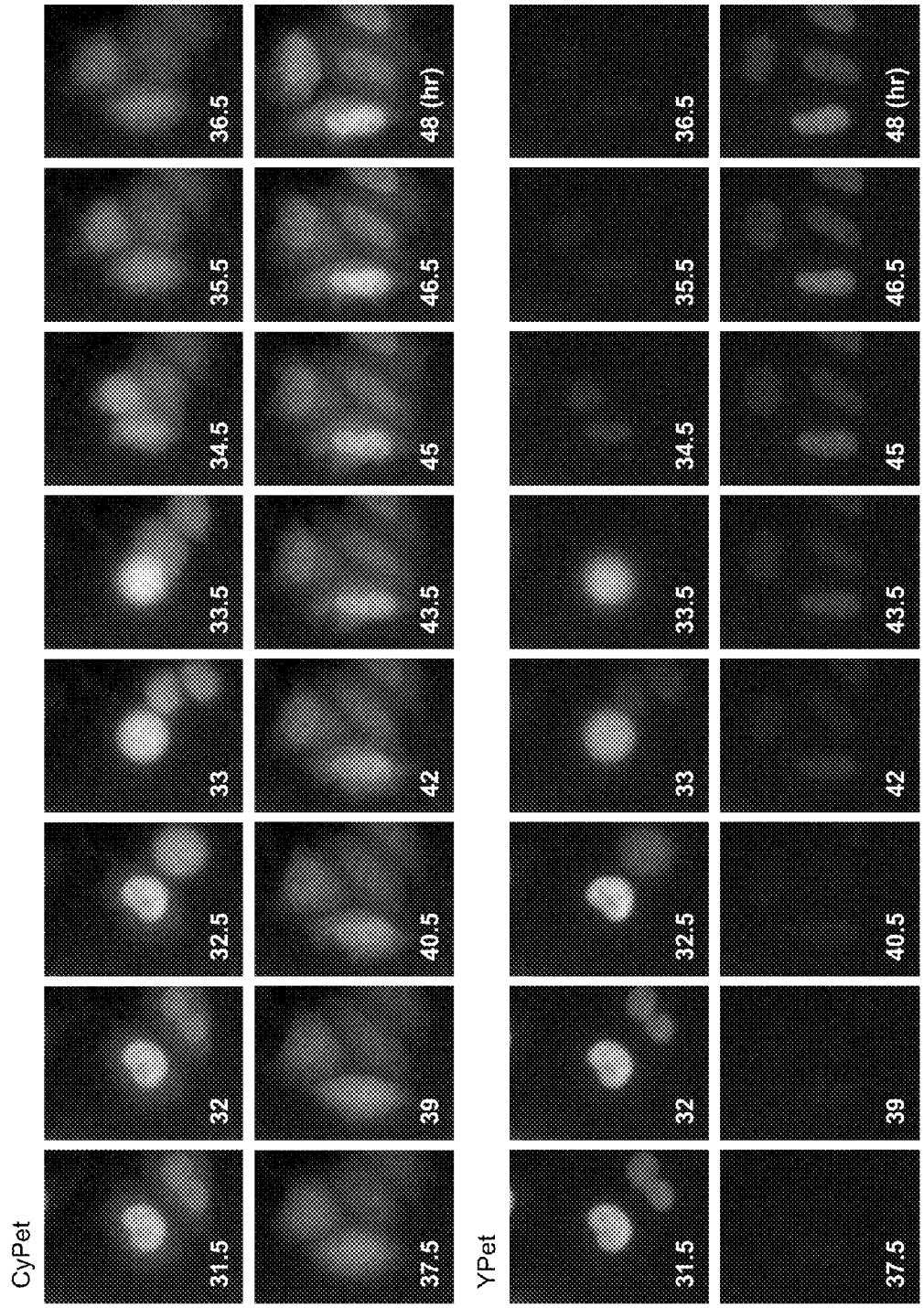
FIG. 7 shows the time-lapse imaging of the Geminin degron probe reagent.

The results are shown in FIG. 6. The value of the fluorescence intensity ratio was rapidly reduced in both the nucleus and the cytoplasm along with cell division. This value showed gradual recovery in the nucleus, but was kept low in the cytoplasm. As a result of observing the fluorescence images of CyPet and YPet by the direct excitation during cell division, the fluorescence of CyPet was constantly observed in the nucleus or the cytoplasm, whereas the fluorescence of YPet rapidly attenuated along with cell division and then showed gradual recovery in the nucleus (FIG. 7). These results demonstrated that the dynamics of Geminin during the process of cell cycle were captured as change in fluorescence associated with the terminated degradation of the probe reagent. Specifically, Geminin (1/110) in the probe reagent is degraded together with YPet in the $G_1$ phase after cell division, while CyPet remains intact by virtue of the degradation-terminating peptide and thus reduces the value of the fluorescence intensity ratio. Then, the degradation of Geminin is suppressed in the $S/G_2/M$ phases, and newly expressed probe reagents accumulate in the nucleus. Thus, the value of the ratio shows recovery. On the other hand, CyPet formed by the limited degradation of the probe reagent is released to the cytoplasm and thus reduces the fluorescence intensity ratio according to cell division. However, new probe reagents do not accumulate therein. This seems to be the reason why the value of the ratio was kept low.

Example 3

<Probe Reagent Comprising IκBα as Degron Protein>

A probe reagent comprising IκBα as a degron protein was prepared for monitoring the activity of the transcription factor NFκB on the basis of proteolytic activity thereon. The protein IκBα binds to NFκB in the cytoplasm to inhibit its nuclear transfer and transcriptional activity. When cells receive signals activating NFκB, IκB kinase is activated to phosphorylate IκBα. The phosphorylated IκBα is ubiquitinated by ubiquitin ligase and degraded by proteasome. As a result, suppression against NFκB is canceled so that it transfers to the nucleus and activates gene transcription. The constant activation of NF-κB has been reported so far in malignant tumor cells or autoimmune disease. Thus, such an assay system can probably be applied to the development of diagnosis or therapeutic drugs for these diseases.

Figure 8:
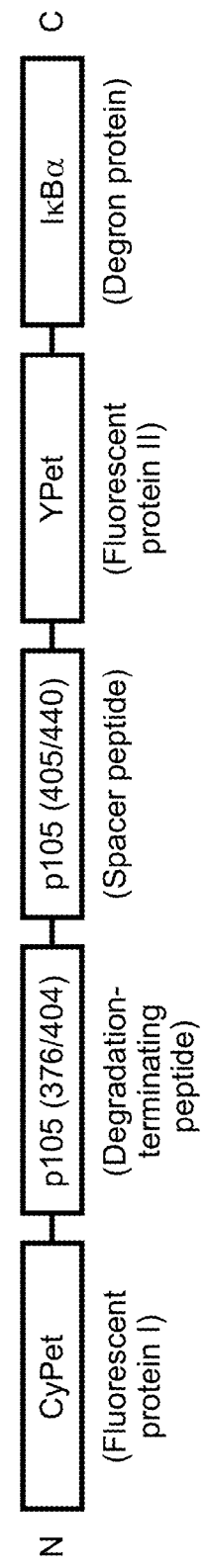
FIG. 8 shows the structure of an IκBα degron probe reagent.

CyPet as a fluorescent protein I, YPet as a fluorescent protein II, full-length IκBα as a degron protein, p105 (376/404) as a degradation-terminating peptide, and p105 (405/440) as a spacer peptide were used as the components of a probe reagent. The degron protein Geminin (1/110) in the probe reagent for screening for a degradation-terminating peptide described above was replaced by human- or mouse-derived IκBα (human: NM_020529, NM_003340, or NM_003339, mouse: AF112979) to prepare a probe reagent (FIG. 8).

Cos7 cells were cultured in a Dulbecco's modified Eagle's medium containing 10% fetal bovine serum in a 35 mmϕ glass-bottomed dish. In the same way as in the experiment to screen for a degradation-terminating peptide, the cells were transfected with the gene DNA of the probe reagent and imaged using an incubator microscope. Images were obtained every 10 minutes for 2 hours. Ten minutes after beginning of the imaging, TNF-α was added as an NFκB activator at a concentration of 20 ng/ml to the medium.

Figure 9:
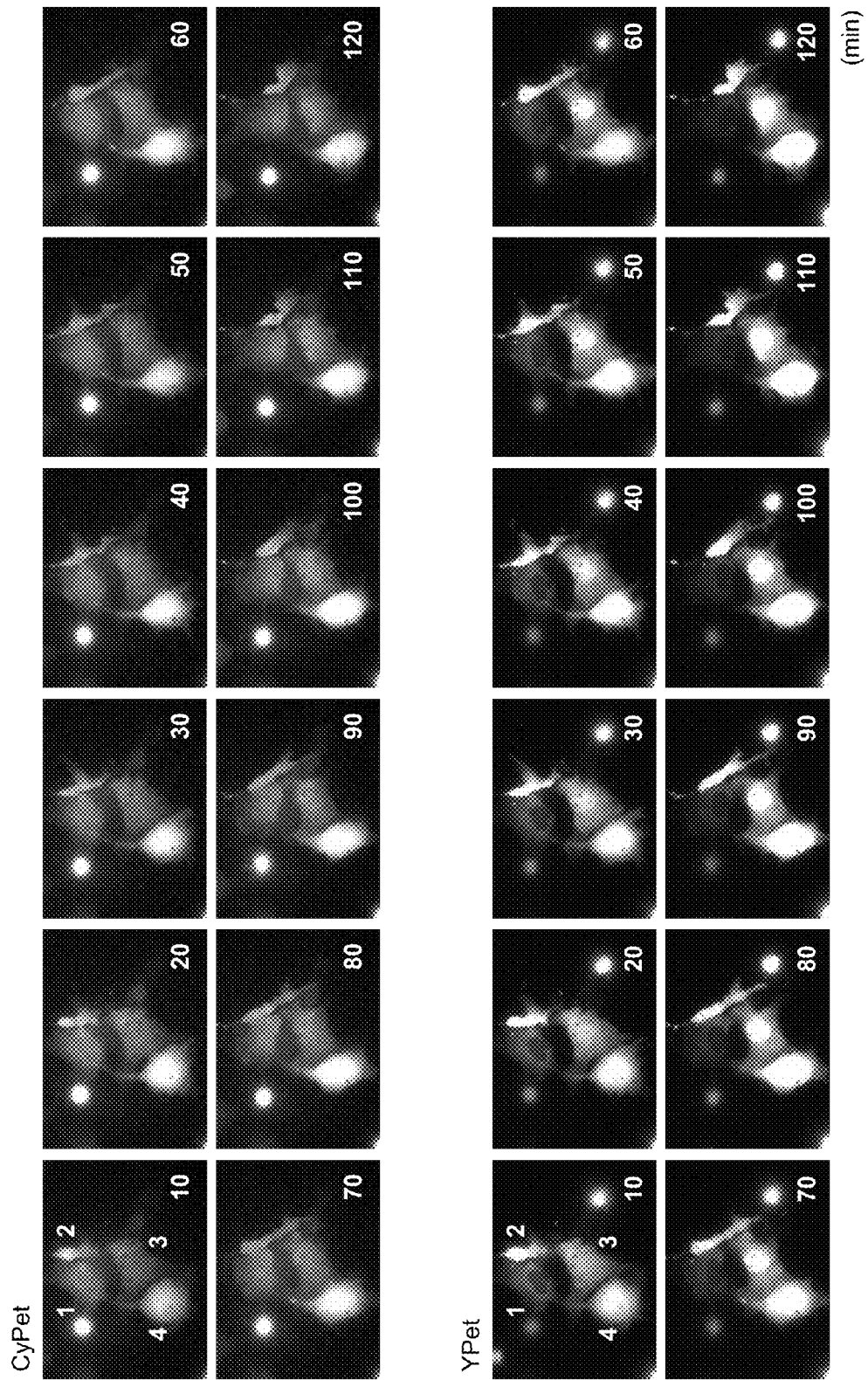
FIG. 9 shows the time-lapse imaging of the IκBα degron probe reagent.
Figure 10:
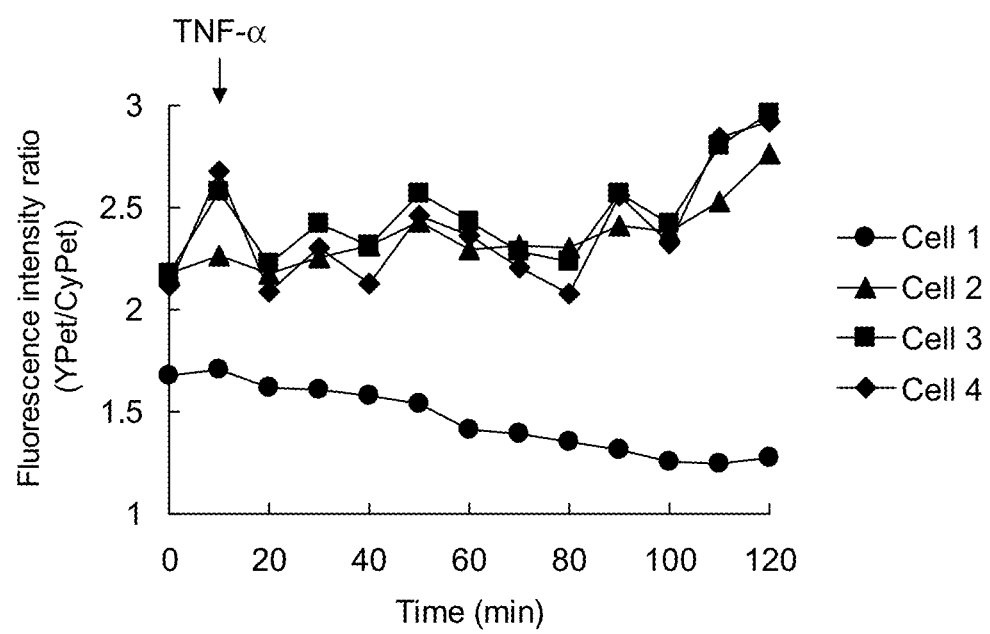
FIG. 10 shows the time-dependent change in the fluorescence intensity ratio of the IκBα degron probe reagent in cell Nos. 1 to 4.

Of the obtained images, time-dependent change in the fluorescence image of CyPet from CyPet excitation and in the fluorescence image of YPet from YPet excitation is shown in FIG. 9. One (No. 1) out of four cells in view exhibited response, and fluorescence intensity was reduced only in YPet. Along with this, reduction in YPet/CyPet fluorescence intensity ratio at the time of CyPet excitation was observed (FIG. 10). This result demonstrated that this probe reagent was able to visualize the degradation process of IκBα mediated by TNF-= stimulation as change in fluorescence.

INDUSTRIAL APPLICABILITY

The probe reagent of the present invention will be able to contribute to the development of therapies or drugs for diseases caused by abnormalities in the ubiquitin-proteasome system by measuring proteolytic activities on proteins associated with the disease in cells or animal individuals.

Free Text for Sequence Listing
SEQ ID NO: 13: Synthetic peptide
SEQ ID NO: 14: DNA encoding synthetic peptide
SEQ ID NO: 15: CyPet-derived peptide All publications, patents, and patent applications cited herein are incorporated herein by reference in their entirety.

The invention claimed is:

1. A probe reagent comprising, in order from the N-terminus to the C-terminus, the amino acid sequences of:
   (1) a fluorescent protein I;
   (2) a peptide capable of terminating protein degradation, which is a degradation-terminating peptide derived from p105, wherein the degradation-terminating peptide consists essentially of amino acid residues 1-29, 7-29, or 17-29 of SEQ ID NO: 1;
   (3) a spacer peptide, which consists essentially of amino acid residues 30-34, 30-45, 30-59, or 30-65 of SEQ ID NO: 1 or the amino acid sequence of SEQ ID NO: 15;
   (4) a fluorescent protein II; and
   (5) a protein to be degraded,
   wherein the protein to be degraded is a protein degraded by the ubiquitin-proteasome system, and the probe reagent is degraded from the C-terminus but the degradation of the probe reagent is terminated at the degradation-terminating peptide.

2. The probe reagent according to claim 1, wherein the fluorescent protein I and the fluorescent protein II differ in excitation wavelength or fluorescence wavelength, or both.

3. The probe reagent according to claim 1, wherein the fluorescent protein I and the fluorescent protein II are a donor and an acceptor, respectively, of fluorescence energy transfer (FRET).

4. The probe reagent according to claim 1, further comprising a nuclear localization signal or a nuclear export signal.

5. A nucleic acid encoding a probe reagent according to claim 1.

6. A vector comprising a nucleic acid according to claim 5 in an expressible form.

7. A transformed cell comprising a vector according to claim 6.

8. The transformed cell according to claim 7, wherein the transformed cell is a diseased cell.

9. A method for screening a therapeutic agent for a disease associated with abnormality in the ubiquitin-proteasome system, comprising: contacting the probe reagent according to claim 1 with a cell associated with abnormality in the ubiquitin-proteasome system, and a candidate substance; measuring the proteolytic activity of the ubiquitin-proteasome system, and comparing the activity in the presence of a candidate substance with that in the absence of a candidate substance, thereby selecting a candidate substance which controls proteasome activity.

10. The method according to claim 9, wherein the proteolytic activity is measured on the basis of change in the ratio of fluorescence intensity between the fluorescent proteins I and II.

11. The method according to claim 9, wherein the cell is a diseased cell associated with abnormality in the ubiquitin-proteasome system.

12. A method for examining the relationship of an abnormality in the ubiquitin-proteasome system with a disease, comprising contacting the probe reagent according to claim 1 or the vector according to claim 6 with a cell or a cell extract from a patient with the disease, measuring a proteolytic activity on the probe reagent and comparing the measured proteolytic activity with a proteolytic activity from a normal control cell.

13. The method according to claim 9, wherein the protein to be degraded in the probe reagent, is a protein associated with the disease.

14. The probe regent according to claim 1, wherein the degradation-terminating peptide consists of the amino acid residues 376-404 of SEQ ID NO: 17.

15. The probe regent according to claim 1, wherein the spacer peptide consists of the amino acid residues 405-440 of SEQ ID NO: 17.

16. The method of claim 12, wherein the probe reagent or vector further comprise a nuclear localization signal or a nuclear export signal.

* * * * *

```
                        SEQUENCE LISTING

<160> NUMBER OF SEQ ID NOS: 19

<210> SEQ ID NO 1
<211> LENGTH: 65
<212> TYPE: PRT
<213> ORGANISM: Homo sapiens

<400> SEQUENCE: 1

Gly Gly Gly Ser Gly Ala Gly Ala Gly Gly Gly Met Phe Gly Ser
1               5                   10                  15

Gly Gly Gly Gly Gly Gly Thr Gly Ser Thr Gly Pro Gly Tyr Ser Phe
                20                  25                  30

Pro His Tyr Gly Phe Pro Thr Tyr Gly Gly Ile Thr Phe His Pro Gly
            35                  40                  45

Thr Thr Lys Ser Asn Ala Gly Met Lys His Gly Thr Met Asp Thr Glu
        50                  55                  60

Ser
65

<210> SEQ ID NO 2
<211> LENGTH: 195
<212> TYPE: DNA
<213> ORGANISM: Homo sapiens

<400> SEQUENCE: 2
ggcggtggta gtggtgccgg agctggaggc ggaggcatgt ttggtagtgg cggtggagga      60
gggggcactg gaagtacagg tccagggtat agcttcccac actatggatt tcctacttat     120
ggtgggatta ctttccatcc tggaactact aaatctaatg ctgggatgaa gcatggaacc     180
atggacactg aatct                                                      195

<210> SEQ ID NO 3
<211> LENGTH: 59
<212> TYPE: PRT
<213> ORGANISM: Homo sapiens

<400> SEQUENCE: 3

Gly Ala Gly Gly Gly Gly Met Phe Gly Ser Gly Gly Gly Gly Gly Gly
1               5                   10                  15

Thr Gly Ser Thr Gly Pro Gly Tyr Ser Phe Pro His Tyr Gly Phe Pro
                20                  25                  30

Thr Tyr Gly Gly Ile Thr Phe His Pro Gly Thr Thr Lys Ser Asn Ala
            35                  40                  45
```

Gly Met Lys His Gly Thr Met Asp Thr Glu Ser
        50                  55

<210> SEQ ID NO 4
<211> LENGTH: 177
<212> TYPE: DNA
<213> ORGANISM: Homo sapiens

<400> SEQUENCE: 4
ggagctggag gcggaggcat gtttggtagt ggcggtggag gaggggggcac tggaagtaca      60 ggtccagggt atagcttccc acactatgga tttcctactt atggtgggat tactttccat     120
cctggaacta ctaaatctaa tgctgggatg aagcatggaa ccatggacac tgaatct       177

<210> SEQ ID NO 5
<211> LENGTH: 49
<212> TYPE: PRT
<213> ORGANISM: Homo sapiens

<400> SEQUENCE: 5

Gly Gly Gly Gly Gly Gly Thr Gly Ser Thr Gly Pro Gly Tyr Ser Phe
1               5                   10                  15

Pro His Tyr Gly Phe Pro Thr Tyr Gly Gly Ile Thr Phe His Pro Gly
            20                  25                  30

Thr Thr Lys Ser Asn Ala Gly Met Lys His Gly Thr Met Asp Thr Glu
        35                  40                  45

Ser

<210> SEQ ID NO 6
<211> LENGTH: 147
<212> TYPE: DNA
<213> ORGANISM: Homo sapiens

<400> SEQUENCE: 6
ggcggtggag gaggggggcac tggaagtaca ggtccagggt atagcttccc acactatgga     60
tttcctactt atggtgggat tactttccat cctggaacta ctaaatctaa tgctgggatg    120
aagcatggaa ccatggacac tgaatct                                        147

<210> SEQ ID NO 7
<211> LENGTH: 59
<212> TYPE: PRT
<213> ORGANISM: Homo sapiens

<400> SEQUENCE: 7

Gly Gly Gly Ser Gly Ala Gly Ala Gly Gly Gly Met Phe Gly Ser
1               5                   10                  15

Gly Gly Gly Gly Gly Gly Thr Gly Ser Thr Gly Pro Gly Tyr Ser Phe
            20                  25                  30

Pro His Tyr Gly Phe Pro Thr Tyr Gly Gly Ile Thr Phe His Pro Gly
        35                  40                  45

Thr Thr Lys Ser Asn Ala Gly Met Lys His Gly
    50                  55

<210> SEQ ID NO 8
<211> LENGTH: 177
<212> TYPE: DNA
<213> ORGANISM: Homo sapiens

<400> SEQUENCE: 8

```
ggcggtggta gtggtgccgg agctggaggc ggaggcatgt ttggtagtgg cggtggagga     60
gggggcactg gaagtacagg tccagggtat agcttcccac actatggatt cctacttat    120 ggtgggatta ctttccatcc tggaactact aaatctaatg ctgggatgaa gcatgga      177
```

<210> SEQ ID NO 9
<211> LENGTH: 45
<212> TYPE: PRT
<213> ORGANISM: Homo sapiens

<400> SEQUENCE: 9

```
Gly Gly Gly Ser Gly Ala Gly Ala Gly Gly Gly Gly Met Phe Gly Ser
1               5                   10                  15

Gly Gly Gly Gly Gly Gly Thr Gly Ser Thr Gly Pro Gly Tyr Ser Phe
            20                  25                  30

Pro His Tyr Gly Phe Pro Thr Tyr Gly Gly Ile Thr Phe
            35                  40              45
```

<210> SEQ ID NO 10
<211> LENGTH: 135
<212> TYPE: DNA
<213> ORGANISM: Homo sapiens

<400> SEQUENCE: 10

```
ggcggtggta gtggtgccgg agctggaggc ggaggcatgt ttggtagtgg cggtggagga     60
gggggcactg gaagtacagg tccagggtat agcttcccac actatggatt cctacttat    120 ggtgggatta ctttc                                                     135
```

<210> SEQ ID NO 11
<211> LENGTH: 34
<212> TYPE: PRT
<213> ORGANISM: Homo sapiens

<400> SEQUENCE: 11

```
Gly Gly Gly Ser Gly Ala Gly Ala Gly Gly Gly Gly Met Phe Gly Ser
1               5                   10                  15

Gly Gly Gly Gly Gly Gly Thr Gly Ser Thr Gly Pro Gly Tyr Ser Phe
            20                  25                  30

Pro His
```

<210> SEQ ID NO 12
<211> LENGTH: 102
<212> TYPE: DNA
<213> ORGANISM: Homo sapiens

<400> SEQUENCE: 12

```
ggcggtggta gtggtgccgg agctggaggc ggaggcatgt ttggtagtgg cggtggagga     60
gggggcactg gaagtacagg tccagggtat agcttcccac ac                      102
```

<210> SEQ ID NO 13
<211> LENGTH: 59
<212> TYPE: PRT
<213> ORGANISM: Artificial
<220> FEATURE:
<223> OTHER INFORMATION: synthetic peptide

<400> SEQUENCE: 13

```
Gly Gly Gly Ser Gly Ala Gly Ala Gly Gly Gly Gly Met Phe Gly Ser
1               5                   10                  15

Gly Gly Gly Gly Gly Gly Thr Gly Ser Thr Gly Pro Gly Glu Phe Asp
```

```
                  20                  25                  30

Pro Asn Glu Lys Arg Asp His Met Val Leu Leu Glu Phe Val Thr Ala
            35                  40                  45

Ala Gly Ile Thr Leu Gly Met Asp Glu Leu Tyr
        50                  55

<210> SEQ ID NO 14
<211> LENGTH: 177
<212> TYPE: DNA
<213> ORGANISM: Artificial
<220> FEATURE:
<223> OTHER INFORMATION: synthetic peptide coding DNA

<400> SEQUENCE: 14
ggcggtggta gtggtgccgg agctggaggc ggaggcatgt ttggtagtgg cggtggagga        60
gggggcactg gaagtacagg tccaggggaa ttcgacccca cgagaagcg  cgatcacatg       120 gtcctgctgg agttcgtgac cgccgccggg atcactctcg gcatggacga gctgtac         177

<210> SEQ ID NO 15
<211> LENGTH: 30
<212> TYPE: PRT
<213> ORGANISM: Artificial
<220> FEATURE:
<223> OTHER INFORMATION: peptide from CyPet

<400> SEQUENCE: 15

Glu Phe Asp Pro Asn Glu Lys Arg Asp His Met Val Leu Leu Glu Phe
1               5                  10                  15

Val Thr Ala Ala Gly Ile Thr Leu Gly Met Asp Glu Leu Tyr
            20                  25                  30

<210> SEQ ID NO 16
<211> LENGTH: 4093
<212> TYPE: DNA
<213> ORGANISM: Homo sapiens
<220> FEATURE:
<221> NAME/KEY: CDS
<222> LOCATION: (468)..(3377)

<400> SEQUENCE: 16
gtgagagagt gagcgagaca gaaagagaga gaagtgcacc agcgagccgg ggcaggaaga        60
ggaggtttcg ccaccggagc ggcccggcga cgcgctgaca gcttcccctg cccttcccgt       120
cggtcgggcc gccagccgcc gcagccctcg gcctgcacgc agccaccggc cccgctcccg       180
gagcccagcg ccgccgaggc cgcagccgcc cggccagtaa ggcggcgccc ccgcccggcc       240
accgcgcgcc ctgcgcttcc ctccgcccgc gctgcggcca tggcgcggcg ctgactggcc       300
tggcccggcc ccgccgcgct cccgctcgcc ccgaccgcca ctcgggcccg ccgggctcc        360 ggcctgccgc cgcctcttcc ttctccagcc ggcaggcccg cgccgcttag gagggagagc       420
ccacccgcgc caggaggccg aacgcggact cgccacccgg cttcaga atg gca gaa        476
                                                    Met Ala Glu
                                                     1 gat gat cca tat ttg gga agg cct gaa caa atg ttt cat ttg gat cct        524
Asp Asp Pro Tyr Leu Gly Arg Pro Glu Gln Met Phe His Leu Asp Pro
    5                  10                  15 tct ttg act cat aca ata ttt aat cca gaa gta ttt caa cca cag atg        572
Ser Leu Thr His Thr Ile Phe Asn Pro Glu Val Phe Gln Pro Gln Met
20                  25                  30                  35 gca ctg cca aca gca gat ggc cca tac ctt caa ata tta gag caa cct        620
Ala Leu Pro Thr Ala Asp Gly Pro Tyr Leu Gln Ile Leu Glu Gln Pro
```

-continued

| | | | | | | | | | | | | | | | | |
|---|---|---|---|---|---|---|---|---|---|---|---|---|---|---|---|---|
| | | | 40 | | | | 45 | | | | | 50 | | | | |
| aaa | cag | aga | gga | ttt | cgt | ttc | cgt | tat | gta | tgt | gaa | ggc | cca | tcc | cat | 668 |
| Lys | Gln | Arg | Gly | Phe | Arg | Phe | Arg | Tyr | Val | Cys | Glu | Gly | Pro | Ser | His | |
| | | | 55 | | | | | 60 | | | | | 65 | | | |
| ggt | gga | cta | cct | ggt | gcc | tct | agt | gaa | aag | aac | aag | aag | tct | tac | cct | 716 |
| Gly | Gly | Leu | Pro | Gly | Ala | Ser | Ser | Glu | Lys | Asn | Lys | Lys | Ser | Tyr | Pro | |
| | | 70 | | | | | 75 | | | | | 80 | | | | |
| cag | gtc | aaa | atc | tgc | aac | tat | gtg | gga | cca | gca | aag | gtt | att | gtt | cag | 764 |
| Gln | Val | Lys | Ile | Cys | Asn | Tyr | Val | Gly | Pro | Ala | Lys | Val | Ile | Val | Gln | |
| 85 | | | | | 90 | | | | | 95 | | | | | | |
| ttg | gtc | aca | aat | gga | aaa | aat | atc | cac | ctg | cat | gcc | cac | agc | ctg | gtg | 812 |
| Leu | Val | Thr | Asn | Gly | Lys | Asn | Ile | His | Leu | His | Ala | His | Ser | Leu | Val | |
| 100 | | | | | 105 | | | | | 110 | | | | | 115 | |
| gga | aaa | cac | tgt | gag | gat | ggg | atc | tgc | act | gta | act | gct | gga | ccc | aag | 860 |
| Gly | Lys | His | Cys | Glu | Asp | Gly | Ile | Cys | Thr | Val | Thr | Ala | Gly | Pro | Lys | |
| | | | | 120 | | | | | 125 | | | | | 130 | | |
| gac | atg | gtg | gtc | ggc | ttc | gca | aac | ctg | ggt | ata | ctt | cat | gtg | aca | aag | 908 |
| Asp | Met | Val | Val | Gly | Phe | Ala | Asn | Leu | Gly | Ile | Leu | His | Val | Thr | Lys | |
| | | | 135 | | | | | 140 | | | | | 145 | | | |
| aaa | aaa | gta | ttt | gaa | aca | ctg | gaa | gca | cga | atg | aca | gag | gcg | tgt | ata | 956 |
| Lys | Lys | Val | Phe | Glu | Thr | Leu | Glu | Ala | Arg | Met | Thr | Glu | Ala | Cys | Ile | |
| | | 150 | | | | | 155 | | | | | 160 | | | | |
| agg | ggc | tat | aat | cct | gga | ctc | ttg | gtg | cac | cct | gac | ctt | gcc | tat | ttg | 1004 |
| Arg | Gly | Tyr | Asn | Pro | Gly | Leu | Leu | Val | His | Pro | Asp | Leu | Ala | Tyr | Leu | |
| 165 | | | | | 170 | | | | | 175 | | | | | | |
| caa | gca | gaa | ggt | gga | ggg | gac | cgg | cag | ctg | gga | gat | cgg | gaa | aaa | gag | 1052 |
| Gln | Ala | Glu | Gly | Gly | Gly | Asp | Arg | Gln | Leu | Gly | Asp | Arg | Glu | Lys | Glu | |
| 180 | | | | | 185 | | | | | 190 | | | | | 195 | |
| cta | atc | cgc | caa | gca | gct | ctg | cag | cag | acc | aag | gag | atg | gac | ctc | agc | 1100 |
| Leu | Ile | Arg | Gln | Ala | Ala | Leu | Gln | Gln | Thr | Lys | Glu | Met | Asp | Leu | Ser | |
| | | | | 200 | | | | | 205 | | | | | 210 | | |
| gtg | gtg | cgg | ctc | atg | ttt | aca | gct | ttt | ctt | ccg | gat | agc | act | ggc | agc | 1148 |
| Val | Val | Arg | Leu | Met | Phe | Thr | Ala | Phe | Leu | Pro | Asp | Ser | Thr | Gly | Ser | |
| | | | 215 | | | | | 220 | | | | | 225 | | | |
| ttc | aca | agg | cgc | ctg | gaa | ccc | gtg | gta | tca | gac | gcc | atc | tat | gac | agt | 1196 |
| Phe | Thr | Arg | Arg | Leu | Glu | Pro | Val | Val | Ser | Asp | Ala | Ile | Tyr | Asp | Ser | |
| | | 230 | | | | | 235 | | | | | 240 | | | | |
| aaa | gcc | ccc | aat | gca | tcc | aac | ttg | aaa | att | gta | aga | atg | gac | agg | aca | 1244 |
| Lys | Ala | Pro | Asn | Ala | Ser | Asn | Leu | Lys | Ile | Val | Arg | Met | Asp | Arg | Thr | |
| 245 | | | | | 250 | | | | | 255 | | | | | | |
| gct | gga | tgt | gtg | act | gga | ggg | gag | gaa | att | tat | ctt | ctt | tgt | gac | aaa | 1292 |
| Ala | Gly | Cys | Val | Thr | Gly | Gly | Glu | Glu | Ile | Tyr | Leu | Leu | Cys | Asp | Lys | |
| 260 | | | | | 265 | | | | | 270 | | | | | 275 | |
| gtt | cag | aaa | gat | gac | atc | cag | att | cga | ttt | tat | gaa | gag | gaa | gaa | aat | 1340 |
| Val | Gln | Lys | Asp | Asp | Ile | Gln | Ile | Arg | Phe | Tyr | Glu | Glu | Glu | Glu | Asn | |
| | | | | 280 | | | | | 285 | | | | | 290 | | |
| ggt | gga | gtc | tgg | gaa | gga | ttt | gga | gat | ttt | tcc | ccc | aca | gat | gtt | cat | 1388 |
| Gly | Gly | Val | Trp | Glu | Gly | Phe | Gly | Asp | Phe | Ser | Pro | Thr | Asp | Val | His | |
| | | | 295 | | | | | 300 | | | | | 305 | | | |
| aga | caa | ttt | gcc | att | gtc | ttc | aaa | act | cca | aag | tat | aaa | gat | att | aat | 1436 |
| Arg | Gln | Phe | Ala | Ile | Val | Phe | Lys | Thr | Pro | Lys | Tyr | Lys | Asp | Ile | Asn | |
| | | 310 | | | | | 315 | | | | | 320 | | | | |
| att | aca | aaa | cca | gcc | tct | gtg | ttt | gtc | cag | ctt | cgg | agg | aaa | tct | gac | 1484 |
| Ile | Thr | Lys | Pro | Ala | Ser | Val | Phe | Val | Gln | Leu | Arg | Arg | Lys | Ser | Asp | |
| 325 | | | | | 330 | | | | | 335 | | | | | | |
| ttg | gaa | act | agt | gaa | cca | aaa | cct | ttc | ctc | tac | tat | cct | gaa | atc | aaa | 1532 |
| Leu | Glu | Thr | Ser | Glu | Pro | Lys | Pro | Phe | Leu | Tyr | Tyr | Pro | Glu | Ile | Lys | |
| 340 | | | | | 345 | | | | | 350 | | | | | 355 | |
| gat | aaa | gaa | gaa | gtg | cag | agg | aaa | cgt | cag | aag | ctc | atg | ccc | aat | ttt | 1580 |

```
                Asp Lys Glu Glu Val Gln Arg Lys Arg Gln Lys Leu Met Pro Asn Phe
                                360                 365                 370 tcg gat agt ttc ggc ggt ggt agt ggt gct gga gct gga ggc gga ggc                      1628
Ser Asp Ser Phe Gly Gly Gly Ser Gly Ala Gly Ala Gly Gly Gly Gly
            375                 380                 385 atg ttt ggt agt ggc ggt gga gga ggg ggc act gga agt aca ggt cca                      1676
Met Phe Gly Ser Gly Gly Gly Gly Gly Gly Thr Gly Ser Thr Gly Pro
        390                 395                 400 ggg tat agc ttc cca cac tat gga ttt cct act tat ggt ggg att act                      1724
Gly Tyr Ser Phe Pro His Tyr Gly Phe Pro Thr Tyr Gly Gly Ile Thr
    405                 410                 415 ttc cat cct gga act act aaa tct aat gct ggg atg aag cat gga acc                      1772
Phe His Pro Gly Thr Thr Lys Ser Asn Ala Gly Met Lys His Gly Thr
420                 425                 430                 435 atg gac act gaa tct aaa aag gac cct gaa ggt tgt gac aaa agt gat                      1820
Met Asp Thr Glu Ser Lys Lys Asp Pro Glu Gly Cys Asp Lys Ser Asp
                440                 445                 450 gac aaa aac act gta aac ctc ttt ggg aaa gtt att gaa acc aca gag                      1868
Asp Lys Asn Thr Val Asn Leu Phe Gly Lys Val Ile Glu Thr Thr Glu
            455                 460                 465 caa gat cag gag ccc agc gag gcc acc gtt ggg aat ggt gag gtc act                      1916
Gln Asp Gln Glu Pro Ser Glu Ala Thr Val Gly Asn Gly Glu Val Thr
        470                 475                 480 cta acg tat gca aca gga aca aaa gaa gag agt gct gga gtt cag gat                      1964
Leu Thr Tyr Ala Thr Gly Thr Lys Glu Glu Ser Ala Gly Val Gln Asp
    485                 490                 495 aac ctc ttt cta gag aag gct atg cag ctt gca aag agg cat gcc aat                      2012
Asn Leu Phe Leu Glu Lys Ala Met Gln Leu Ala Lys Arg His Ala Asn
500                 505                 510                 515 gcc ctt ttc gac tac gcg gtg aca gga gac gtg aag atg ctg ctg gcc                      2060
Ala Leu Phe Asp Tyr Ala Val Thr Gly Asp Val Lys Met Leu Leu Ala
                520                 525                 530 gtc cag cgc cat ctc act gct gtg cag gat gag aat ggg gac agt gtc                      2108
Val Gln Arg His Leu Thr Ala Val Gln Asp Glu Asn Gly Asp Ser Val
            535                 540                 545 tta cac tta gca atc atc cac ctt cat tct caa ctt gtg agg gat cta                      2156
Leu His Leu Ala Ile Ile His Leu His Ser Gln Leu Val Arg Asp Leu
        550                 555                 560 cta gaa gtc aca tct ggt ttg att tct gat gac att atc aac atg aga                      2204
Leu Glu Val Thr Ser Gly Leu Ile Ser Asp Asp Ile Ile Asn Met Arg
    565                 570                 575 aat gat ctg tac cag acg ccc ttg cac ttg gca gtg atc act aag cag                      2252
Asn Asp Leu Tyr Gln Thr Pro Leu His Leu Ala Val Ile Thr Lys Gln
580                 585                 590                 595 gaa gat gtg gtg gag gat ttg ctg agg gct ggg gcc gac ctg agc ctt                      2300
Glu Asp Val Val Glu Asp Leu Leu Arg Ala Gly Ala Asp Leu Ser Leu
                600                 605                 610 ctg gac cgc ttg ggt aac tct gtt ttg cac cta gct gcc aaa gaa gga                      2348
Leu Asp Arg Leu Gly Asn Ser Val Leu His Leu Ala Ala Lys Glu Gly
            615                 620                 625 cat gat aaa gtt ctc agt atc tta ctc aag cac aaa aag gca gca cta                      2396
His Asp Lys Val Leu Ser Ile Leu Leu Lys His Lys Lys Ala Ala Leu
        630                 635                 640 ctt ctt gac cac ccc aac ggg gac ggt ctg aat gcc att cat cta gcc                      2444
Leu Leu Asp His Pro Asn Gly Asp Gly Leu Asn Ala Ile His Leu Ala
    645                 650                 655 atg atg agc aat agc ctg cca tgt ttg ctg ctg ctg gtg gcc gct ggg                      2492
Met Met Ser Asn Ser Leu Pro Cys Leu Leu Leu Leu Val Ala Ala Gly
660                 665                 670                 675
```

```
gct gac gtc aat gct cag gag cag aag tcc ggg cgc aca gca ctg cac    2540
Ala Asp Val Asn Ala Gln Glu Gln Lys Ser Gly Arg Thr Ala Leu His
            680                 685                 690 ctg gct gtg gag cac gac aac atc tca ttg gca ggc tgc ctg ctc ctg    2588
Leu Ala Val Glu His Asp Asn Ile Ser Leu Ala Gly Cys Leu Leu Leu
    695                 700                 705 gag ggt gat gcc cat gtg gac agt act acc tac gat gga acc aca ccc    2636
Glu Gly Asp Ala His Val Asp Ser Thr Thr Tyr Asp Gly Thr Thr Pro
        710                 715                 720 ctg cat ata gca gct ggg aga ggg tcc acc agg ctg gca gct ctt ctc    2684
Leu His Ile Ala Ala Gly Arg Gly Ser Thr Arg Leu Ala Ala Leu Leu
            725                 730                 735 aaa gca gca gga gca gat ccc ctg gtg gag aac ttt gag cct ctc tat    2732
Lys Ala Ala Gly Ala Asp Pro Leu Val Glu Asn Phe Glu Pro Leu Tyr
740                 745                 750                 755 gac ctg gat gac tct tgg gaa aat gca gga gag gat gaa gga gtt gtg    2780
Asp Leu Asp Asp Ser Trp Glu Asn Ala Gly Glu Asp Glu Gly Val Val
        760                 765                 770 cct gga acc acg cct cta gat atg gcc acc agc tgg cag gta ttt gac    2828
Pro Gly Thr Thr Pro Leu Asp Met Ala Thr Ser Trp Gln Val Phe Asp
            775                 780                 785 ata tta aat ggg aaa cca tat gag cca gag ttt aca tct gat gat tta    2876
Ile Leu Asn Gly Lys Pro Tyr Glu Pro Glu Phe Thr Ser Asp Asp Leu
        790                 795                 800 cta gca caa gga gac atg aaa cag ctg gct gaa gat gtg aag ctg cag    2924
Leu Ala Gln Gly Asp Met Lys Gln Leu Ala Glu Asp Val Lys Leu Gln
    805                 810                 815 ctg tat aag tta cta gaa att cct gat cca gac aaa aac tgg gct act    2972
Leu Tyr Lys Leu Leu Glu Ile Pro Asp Pro Asp Lys Asn Trp Ala Thr
820                 825                 830                 835 ctg gcg cag aaa tta ggt ctg ggg ata ctt aat aat gcc ttc cgg ctg    3020
Leu Ala Gln Lys Leu Gly Leu Gly Ile Leu Asn Asn Ala Phe Arg Leu
        840                 845                 850 agt cct gct cct tcc aaa aca ctt atg gac aac tat gag gtc tct ggg    3068
Ser Pro Ala Pro Ser Lys Thr Leu Met Asp Asn Tyr Glu Val Ser Gly
            855                 860                 865 ggt aca gtc aga gag ctg gtg gag gcc ctg aga caa atg ggc tac acc    3116
Gly Thr Val Arg Glu Leu Val Glu Ala Leu Arg Gln Met Gly Tyr Thr
        870                 875                 880 gaa gca att gaa gtg atc cag gca gcc tcc agc cca gtg aag acc acc    3164
Glu Ala Ile Glu Val Ile Gln Ala Ala Ser Ser Pro Val Lys Thr Thr
    885                 890                 895 tct cag gcc cac tcg ctg cct ctc tcg cct gcc tcc aca agg cag caa    3212
Ser Gln Ala His Ser Leu Pro Leu Ser Pro Ala Ser Thr Arg Gln Gln
900                 905                 910                 915 ata gac gag ctc cga gac agt gac agt gtc tgc gac agc ggc gtg gag    3260
Ile Asp Glu Leu Arg Asp Ser Asp Ser Val Cys Asp Ser Gly Val Glu
        920                 925                 930 aca tcc ttc cgc aaa ctc agc ttt acc gag tct ctg acc agt ggt gcc    3308
Thr Ser Phe Arg Lys Leu Ser Phe Thr Glu Ser Leu Thr Ser Gly Ala
            935                 940                 945 tca ctg cta act ctc aac aaa atg ccc cat gat tat ggg cag gaa gga    3356
Ser Leu Leu Thr Leu Asn Lys Met Pro His Asp Tyr Gly Gln Glu Gly
        950                 955                 960 cct cta gaa ggc aaa att tag cctgctgaca atttcccaca ccgtgtaaac       3407
Pro Leu Glu Gly Lys Ile
    965 caaagcccta aaattccact gcgttgtcca caagacagaa gctgaagtgc atccaaaggt  3467 gctcagagag ccggcccgcc tgaatcattc tcgatttaac tcgagacctt ttcaacttgg  3527
```

-continued

```
cttcctttct tggttcataa atgaattta gtttggttca cttacagata gtatctagca    3587
atcacaacac tggctgagcg gatgcatctg gggatgaggt tgcttactaa gctttgccag    3647
ctgctgctgg atcacagctg ctttctgttg tcattgctgt tgtccctctg ctacgttcct    3707
attgtcatta aaggtatcac ggtcgccacc tggcattcct tctgaccaca gcatcatttt    3767
gcattcaaat taagggttaa gaaaagagat attttaaaat gagagtcact tgatgtgcca    3827
ttttaaaaaa aaaggcatat tgcttttct aatgtggtta tttctctgat ttgcaaaaaa    3887
aaaaaaaaaa aaaatacttg tcaatattta acatggtta caatcattgc tgaaaatggt    3947
attttccccc ttttctgcat tttgctattg taaatatgtt ttttagatca aatactttaa    4007
aggaaaaaat gttggattta taaatgctat tttttatttt acttttataa taaaaggaaa    4067
agcaaattga tgacctcaaa aaaaaa                                         4093
```

<210> SEQ ID NO 17
<211> LENGTH: 969
<212> TYPE: PRT
<213> ORGANISM: Homo sapiens

<400> SEQUENCE: 17

```
Met Ala Glu Asp Asp Pro Tyr Leu Gly Arg Pro Glu Gln Met Phe His
1               5                   10                  15

Leu Asp Pro Ser Leu Thr His Thr Ile Phe Asn Pro Glu Val Phe Gln
                20                  25                  30

Pro Gln Met Ala Leu Pro Thr Ala Asp Gly Pro Tyr Leu Gln Ile Leu
            35                  40                  45

Glu Gln Pro Lys Gln Arg Gly Phe Arg Phe Arg Tyr Val Cys Glu Gly
        50                  55                  60

Pro Ser His Gly Gly Leu Pro Gly Ala Ser Ser Glu Lys Asn Lys Lys
    65                  70                  75                  80

Ser Tyr Pro Gln Val Lys Ile Cys Asn Tyr Val Gly Pro Ala Lys Val
                85                  90                  95

Ile Val Gln Leu Val Thr Asn Gly Lys Asn Ile His Leu His Ala His
                100                 105                 110

Ser Leu Val Gly Lys His Cys Glu Asp Gly Ile Cys Thr Val Thr Ala
            115                 120                 125

Gly Pro Lys Asp Met Val Val Gly Phe Ala Asn Leu Gly Ile Leu His
        130                 135                 140

Val Thr Lys Lys Lys Val Phe Glu Thr Leu Glu Ala Arg Met Thr Glu
145                 150                 155                 160

Ala Cys Ile Arg Gly Tyr Asn Pro Gly Leu Leu Val His Pro Asp Leu
                165                 170                 175

Ala Tyr Leu Gln Ala Glu Gly Gly Gly Asp Arg Gln Leu Gly Asp Arg
            180                 185                 190

Glu Lys Glu Leu Ile Arg Gln Ala Ala Leu Gln Gln Thr Lys Glu Met
        195                 200                 205

Asp Leu Ser Val Val Arg Leu Met Phe Thr Ala Phe Leu Pro Asp Ser
    210                 215                 220

Thr Gly Ser Phe Thr Arg Arg Leu Glu Pro Val Val Ser Asp Ala Ile
225                 230                 235                 240

Tyr Asp Ser Lys Ala Pro Asn Ala Ser Asn Leu Lys Ile Val Arg Met
                245                 250                 255

Asp Arg Thr Ala Gly Cys Val Thr Gly Gly Glu Glu Ile Tyr Leu Leu
            260                 265                 270
```

```
Cys Asp Lys Val Gln Lys Asp Ile Gln Ile Arg Phe Tyr Glu Glu
        275                 280                 285
Glu Glu Asn Gly Gly Val Trp Glu Gly Phe Gly Asp Phe Ser Pro Thr
    290                 295                 300
Asp Val His Arg Gln Phe Ala Ile Val Phe Lys Thr Pro Lys Tyr Lys
305                 310                 315                 320
Asp Ile Asn Ile Thr Lys Pro Ala Ser Val Phe Val Gln Leu Arg Arg
                325                 330                 335
Lys Ser Asp Leu Glu Thr Ser Glu Pro Lys Pro Phe Leu Tyr Tyr Pro
            340                 345                 350
Glu Ile Lys Asp Lys Glu Val Gln Arg Lys Gln Lys Leu Met
        355                 360                 365
Pro Asn Phe Ser Asp Ser Phe Gly Gly Ser Gly Ala Gly Ala Gly
    370                 375                 380
Gly Gly Gly Met Phe Gly Gly Gly Gly Gly Thr Gly Ser
385                 390                 395                 400
Thr Gly Pro Gly Tyr Ser Phe Pro His Tyr Gly Phe Pro Thr Tyr Gly
                405                 410                 415
Gly Ile Thr Phe His Pro Gly Thr Thr Lys Ser Asn Ala Gly Met Lys
            420                 425                 430
His Gly Thr Met Asp Thr Glu Ser Lys Lys Asp Pro Glu Gly Cys Asp
        435                 440                 445
Lys Ser Asp Asp Lys Asn Thr Val Asn Leu Phe Gly Lys Val Ile Glu
450                 455                 460
Thr Thr Glu Gln Asp Gln Glu Pro Ser Glu Ala Thr Val Gly Asn Gly
465                 470                 475                 480
Glu Val Thr Leu Thr Tyr Ala Thr Gly Thr Lys Glu Glu Ser Ala Gly
                485                 490                 495
Val Gln Asp Asn Leu Phe Leu Glu Lys Ala Met Gln Leu Ala Lys Arg
            500                 505                 510
His Ala Asn Ala Leu Phe Asp Tyr Ala Val Thr Gly Asp Val Lys Met
        515                 520                 525
Leu Leu Ala Val Gln Arg His Leu Thr Ala Val Gln Asp Glu Asn Gly
    530                 535                 540
Asp Ser Val Leu His Leu Ala Ile Ile His Leu His Ser Gln Leu Val
545                 550                 555                 560
Arg Asp Leu Leu Glu Val Thr Ser Gly Leu Ile Ser Asp Asp Ile Ile
                565                 570                 575
Asn Met Arg Asn Asp Leu Tyr Gln Thr Pro Leu His Leu Ala Val Ile
            580                 585                 590
Thr Lys Gln Glu Asp Val Val Glu Asp Leu Leu Arg Ala Gly Ala Asp
        595                 600                 605
Leu Ser Leu Leu Asp Arg Leu Gly Asn Ser Val Leu His Leu Ala Ala
    610                 615                 620
Lys Glu Gly His Asp Lys Val Leu Ser Ile Leu Leu Lys His Lys Lys
625                 630                 635                 640
Ala Ala Leu Leu Leu Asp His Pro Asn Gly Asp Gly Leu Asn Ala Ile
                645                 650                 655
His Leu Ala Met Met Ser Asn Ser Leu Pro Cys Leu Leu Leu Leu Val
            660                 665                 670
Ala Ala Gly Ala Asp Val Asn Ala Gln Glu Gln Lys Ser Gly Arg Thr
        675                 680                 685
```

```
Ala Leu His Leu Ala Val Glu His Asp Asn Ile Ser Leu Ala Gly Cys
    690                 695                 700

Leu Leu Leu Glu Gly Asp Ala His Val Asp Ser Thr Thr Tyr Asp Gly
705                 710                 715                 720

Thr Thr Pro Leu His Ile Ala Ala Gly Arg Gly Ser Thr Arg Leu Ala
                725                 730                 735

Ala Leu Leu Lys Ala Ala Gly Ala Asp Pro Leu Val Glu Asn Phe Glu
            740                 745                 750

Pro Leu Tyr Asp Leu Asp Asp Ser Trp Glu Asn Ala Gly Glu Asp Glu
        755                 760                 765

Gly Val Val Pro Gly Thr Thr Pro Leu Asp Met Ala Thr Ser Trp Gln
770                 775                 780

Val Phe Asp Ile Leu Asn Gly Lys Pro Tyr Glu Pro Glu Phe Thr Ser
785                 790                 795                 800

Asp Asp Leu Leu Ala Gln Gly Asp Met Lys Gln Leu Ala Glu Asp Val
                805                 810                 815

Lys Leu Gln Leu Tyr Lys Leu Leu Glu Ile Pro Asp Pro Asp Lys Asn
            820                 825                 830

Trp Ala Thr Leu Ala Gln Lys Leu Gly Leu Gly Ile Leu Asn Asn Ala
        835                 840                 845

Phe Arg Leu Ser Pro Ala Pro Ser Lys Thr Leu Met Asp Asn Tyr Glu
850                 855                 860

Val Ser Gly Gly Thr Val Arg Glu Leu Val Glu Ala Leu Arg Gln Met
865                 870                 875                 880

Gly Tyr Thr Glu Ala Ile Glu Val Ile Gln Ala Ala Ser Ser Pro Val
                885                 890                 895

Lys Thr Thr Ser Gln Ala His Ser Leu Pro Leu Ser Pro Ala Ser Thr
            900                 905                 910

Arg Gln Gln Ile Asp Glu Leu Arg Asp Ser Asp Ser Val Cys Asp Ser
        915                 920                 925

Gly Val Glu Thr Ser Phe Arg Lys Leu Ser Phe Thr Glu Ser Leu Thr
930                 935                 940

Ser Gly Ala Ser Leu Leu Thr Leu Asn Lys Met Pro His Asp Tyr Gly
945                 950                 955                 960

Gln Glu Gly Pro Leu Glu Gly Lys Ile
                965

<210> SEQ ID NO 18
<211> LENGTH: 1215
<212> TYPE: DNA
<213> ORGANISM: Homo sapiens
<220> FEATURE:
<221> NAME/KEY: CDS
<222> LOCATION: (335)..(964)

<400> SEQUENCE: 18
cgtcagttgg tcacgtggtt gttcggagcg ggcgagcgga gttagcaggg ctttactgca      60
gagcgcgccg ggcactccag cgaccgtggg gatcagcgta ggtgagctgt ggccttttgc     120
gaggtgctgc agccatagct acgtgcgttc gctacgagga ttgagcgtct ccacccagta     180
agtgggcaag aggcggcagg aagtgggtac gcaggggcgc aagcgcaca gcctctagac      240 gactcgcttt ccctccggcc aacctctgaa gccgcgtcct actttgacag ctgcagggcc     300
gcggcctggt cttctgtgct tcaccatcta cata atg aat ccc agt atg aag cag    355
                                    Met Asn Pro Ser Met Lys Gln
                                      1               5
```

-continued

| | | | | | | | | | | | | | | | |
|---|---|---|---|---|---|---|---|---|---|---|---|---|---|---|---|
| aaa | caa | gaa | gaa | atc | aaa | gag | aat | ata | aag | aat | agt | tct | gtc | cca | aga | 403 |
| Lys | Gln | Glu | Glu | Ile | Lys | Glu | Asn | Ile | Lys | Asn | Ser | Ser | Val | Pro | Arg | |
| | | 10 | | | | | 15 | | | | | 20 | | | | |

| aga | act | ctg | aag | atg | att | cag | cct | tct | gca | tct | gga | tct | ctt | gtt | gga | 451 |
| Arg | Thr | Leu | Lys | Met | Ile | Gln | Pro | Ser | Ala | Ser | Gly | Ser | Leu | Val | Gly | |
| 25 | | | | | 30 | | | | | 35 | | | | | | |

| aga | gaa | aat | gag | ctg | tcc | gca | ggc | ttg | tcc | aaa | agg | aaa | cat | cgg | aat | 499 |
| Arg | Glu | Asn | Glu | Leu | Ser | Ala | Gly | Leu | Ser | Lys | Arg | Lys | His | Arg | Asn | |
| 40 | | | | | 45 | | | | | 50 | | | | | 55 | |

| gac | cac | tta | aca | tct | aca | act | tcc | agc | cct | ggg | gtt | att | gtc | cca | gaa | 547 |
| Asp | His | Leu | Thr | Ser | Thr | Thr | Ser | Ser | Pro | Gly | Val | Ile | Val | Pro | Glu | |
| | | | | 60 | | | | | 65 | | | | | 70 | | |

| tct | agt | gaa | aat | aaa | aat | ctt | gga | gga | gtc | acc | cag | gag | tca | ttt | gat | 595 |
| Ser | Ser | Glu | Asn | Lys | Asn | Leu | Gly | Gly | Val | Thr | Gln | Glu | Ser | Phe | Asp | |
| | | | 75 | | | | | 80 | | | | | 85 | | | |

| ctt | atg | att | aaa | gaa | aat | cca | tcc | tct | cag | tat | tgg | aag | gaa | gtg | gca | 643 |
| Leu | Met | Ile | Lys | Glu | Asn | Pro | Ser | Ser | Gln | Tyr | Trp | Lys | Glu | Val | Ala | |
| | 90 | | | | | 95 | | | | | 100 | | | | | |

| gaa | aaa | cgg | aga | aag | gcg | ctg | tat | gaa | gca | ctt | aag | gaa | aat | gag | aaa | 691 |
| Glu | Lys | Arg | Arg | Lys | Ala | Leu | Tyr | Glu | Ala | Leu | Lys | Glu | Asn | Glu | Lys | |
| 105 | | | | | 110 | | | | | 115 | | | | | | |

| ctt | cat | aaa | gaa | att | gaa | caa | aag | gac | aat | gaa | att | gcc | cgc | ctg | aaa | 739 |
| Leu | His | Lys | Glu | Ile | Glu | Gln | Lys | Asp | Asn | Glu | Ile | Ala | Arg | Leu | Lys | |
| 120 | | | | | 125 | | | | | 130 | | | | | 135 | |

| aag | gag | aat | aaa | gaa | ctg | gca | gaa | gta | gca | gaa | cat | gta | cag | tat | atg | 787 |
| Lys | Glu | Asn | Lys | Glu | Leu | Ala | Glu | Val | Ala | Glu | His | Val | Gln | Tyr | Met | |
| | | | | 140 | | | | | 145 | | | | | 150 | | |

| gca | gag | cta | ata | gag | aga | ctg | aat | ggt | gaa | cct | ctg | gat | aat | ttt | gaa | 835 |
| Ala | Glu | Leu | Ile | Glu | Arg | Leu | Asn | Gly | Glu | Pro | Leu | Asp | Asn | Phe | Glu | |
| | | | 155 | | | | | 160 | | | | | 165 | | | |

| tca | ctg | gat | aat | cag | gaa | ttt | gat | tct | gaa | gaa | gaa | act | gtt | gag | gat | 883 |
| Ser | Leu | Asp | Asn | Gln | Glu | Phe | Asp | Ser | Glu | Glu | Glu | Thr | Val | Glu | Asp | |
| | | 170 | | | | | 175 | | | | | 180 | | | | |

| tct | cta | gtg | gaa | gac | tca | gaa | att | ggc | acg | tgt | gct | gaa | gga | act | gta | 931 |
| Ser | Leu | Val | Glu | Asp | Ser | Glu | Ile | Gly | Thr | Cys | Ala | Glu | Gly | Thr | Val | |
| | 185 | | | | | 190 | | | | | 195 | | | | | |

| tct | tcc | tct | acg | gat | gca | aag | cca | tgt | ata | tga | aatgcattaa | tatttgactg | | | | 984 |
| Ser | Ser | Ser | Thr | Asp | Ala | Lys | Pro | Cys | Ile | | | | | | | |
| 200 | | | | | 205 | | | | | | | | | | | | ttgagaattt tactgccgaa gtttacctcc actagttctt tgtagcagag tacataacta 1044 cataatgcca actctggaat caaatttcct tgtttgaatc ctgggaccct attgcattaa 1104 agtacaaata ctatgtattt ttaatctatg atggtttatg tgaataggat tttctcagtt 1164 gtcagccatg acttatgttt attactaaat aaacttcaaa ctcctgttga a 1215

<210> SEQ ID NO 19
<211> LENGTH: 209
<212> TYPE: PRT
<213> ORGANISM: Homo sapiens

<400> SEQUENCE: 19

Met Asn Pro Ser Met Lys Gln Lys Gln Glu Glu Ile Lys Glu Asn Ile
1               5                   10                  15

Lys Asn Ser Ser Val Pro Arg Arg Thr Leu Lys Met Ile Gln Pro Ser
            20                  25                  30

Ala Ser Gly Ser Leu Val Gly Arg Glu Asn Glu Leu Ser Ala Gly Leu
        35                  40                  45

Ser Lys Arg Lys His Arg Asn Asp His Leu Thr Ser Thr Thr Ser Ser
    50                  55                  60

```
Pro Gly Val Ile Val Pro Glu Ser Ser Glu Asn Lys Asn Leu Gly Gly
 65              70                  75                  80

Val Thr Gln Glu Ser Phe Asp Leu Met Ile Lys Glu Asn Pro Ser Ser
                 85                  90                  95

Gln Tyr Trp Lys Glu Val Ala Glu Lys Arg Arg Lys Ala Leu Tyr Glu
            100                 105                 110

Ala Leu Lys Glu Asn Glu Lys Leu His Lys Glu Ile Glu Gln Lys Asp
            115                 120                 125

Asn Glu Ile Ala Arg Leu Lys Lys Glu Asn Lys Glu Leu Ala Glu Val
        130                 135                 140

Ala Glu His Val Gln Tyr Met Ala Glu Leu Ile Glu Arg Leu Asn Gly
145                 150                 155                 160

Glu Pro Leu Asp Asn Phe Glu Ser Leu Asp Asn Gln Glu Phe Asp Ser
                165                 170                 175

Glu Glu Glu Thr Val Glu Asp Ser Leu Val Glu Asp Ser Glu Ile Gly
            180                 185                 190

Thr Cys Ala Glu Gly Thr Val Ser Ser Ser Thr Asp Ala Lys Pro Cys
            195                 200                 205

Ile
```